(12) United States Patent
Kang et al.

(10) Patent No.: US 10,621,308 B2
(45) Date of Patent: Apr. 14, 2020

(54) ELECTRONIC DEVICE AND METHOD FOR LINKING EXERCISE SCHEDULE THEREOF

(71) Applicant: SAMSUNG ELECTRONICS CO., LTD., Suwon-si, Gyeonggi-do (KR)

(72) Inventors: Seung Seok Kang, Seoul (KR); Jeong Ja Kim, Suwon-si (KR); Kyung Sub Min, Seongnam-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 34 days.

(21) Appl. No.: 15/390,022

(22) Filed: Dec. 23, 2016

(65) Prior Publication Data

US 2017/0185750 A1 Jun. 29, 2017

(30) Foreign Application Priority Data

Dec. 23, 2015 (KR) .................. 10-2015-0184770

(51) Int. Cl.
*H04W 88/04* (2009.01)
*G06F 19/00* (2018.01)
(Continued)

(52) U.S. Cl.
CPC ..... *G06F 19/3481* (2013.01); *G06Q 10/1097* (2013.01); *H04L 67/1095* (2013.01); *H04B 1/385* (2013.01); *H04W 88/04* (2013.01)

(58) Field of Classification Search
CPC ...... G06F 19/3481; G06F 1/163; G06F 21/32; G06F 21/34; G06F 21/60; G06F 21/6218;
(Continued)

(56) References Cited

U.S. PATENT DOCUMENTS 6,921,351 B1 * 7/2005 Hickman ............ G06F 19/3481
482/8
8,529,409 B1 * 9/2013 Lesea-Ames .................. 482/9
(Continued)

FOREIGN PATENT DOCUMENTS

KR 10-2015-0084255 7/2015

OTHER PUBLICATIONS

Rein, How to Get More out of Your Garmin Watch; 2015, pp. 1-8 (Year: 2015).*
(Continued)

*Primary Examiner* — Backhean Tiv
*Assistant Examiner* — Linh T. Nguyen
(74) *Attorney, Agent, or Firm* — Nixon & Vanderhye, P.C.

(57) ABSTRACT

An electronic device is provided. The electronic device includes a communication circuit configured to perform wireless communication, a memory configured to store an exercise schedule to be divided into a plurality of segments, and a processor configured to electrically connect with the communication circuit and the memory. The processor is configured to send a segment automatically selected based on at least one of a policy defined in the electronic device or attributes of an external device from among the plurality of segments included in the exercise schedule to the external device, if the electronic device connects with the external device through the wireless communication and to receive an exercise record collected by the external device from the external device, if the electronic device connects with the external device again through the wireless communication after the wireless communication is disconnected.

19 Claims, 13 Drawing Sheets

(51) Int. Cl.
*G06Q 10/10* (2012.01)
*H04L 29/08* (2006.01)
*H04B 1/3827* (2015.01)

(58) Field of Classification Search
CPC ............ G06Q 10/06311; G06Q 10/10; G06Q 10/1093; H04M 2250/04; H04M 2250/02; A61B 5/0002; A61B 5/11; A61B 5/024; A61B 2503/10; A61B 5/0402; A61B 5/02405; A63B 24/0062; A63B 24/00; H04W 12/08; H04W 12/00; H04W 12/0802; H04W 12/06; H04W 88/02; H04L 67/30; H04L 67/306; A61L 35/11
USPC ........ 482/8, 9, 901, 1, 4, 902; 600/301, 508, 600/595, 534; 709/203, 217, 219
See application file for complete search history.

(56) References Cited

U.S. PATENT DOCUMENTS

| | | | | |
|---|---|---|---|---|
| 9,157,742 | B1* | 10/2015 | Fahrner | G01C 21/00 |
| 2005/0010426 | A1* | 1/2005 | Chen | G06Q 10/02 |
| | | | | 482/8 |
| 2007/0149362 | A1 | 6/2007 | Lee et al. | |
| 2008/0096726 | A1* | 4/2008 | Riley | A63B 24/0006 |
| | | | | 482/8 |
| 2010/0062905 | A1* | 3/2010 | Rottler | G01R 35/005 |
| | | | | 482/9 |
| 2010/0292600 | A1* | 11/2010 | DiBenedetto | A63B 24/0062 |
| | | | | 600/520 |
| 2011/0172059 | A1* | 7/2011 | Watterson | A63B 22/02 |
| | | | | 482/5 |
| 2012/0253485 | A1 | 10/2012 | Weast et al. | |
| 2012/0258433 | A1* | 10/2012 | Hope | G06F 19/3481 |
| | | | | 434/247 |
| 2013/0041771 | A1* | 2/2013 | Soelberg | H04L 63/08 |
| | | | | 705/26.1 |
| 2013/0150987 | A1* | 6/2013 | Mikan | A63B 24/0062 |
| | | | | 700/91 |
| 2014/0056437 | A1* | 2/2014 | DiBenedetto | A63B 24/0062 |
| | | | | 381/77 |
| 2014/0067097 | A1* | 3/2014 | Harris | A63B 71/06 |
| | | | | 700/91 |
| 2014/0081434 | A1* | 3/2014 | Su | H04M 1/7253 |
| | | | | 700/91 |
| 2015/0133748 | A1* | 5/2015 | Edmonds | A61B 5/222 |
| | | | | 600/301 |
| 2016/0147968 | A1* | 5/2016 | Coney | G06F 19/3406 |
| | | | | 705/2 |
| 2016/0220867 | A1* | 8/2016 | Flaherty | G06F 19/3481 |
| 2016/0346617 | A1* | 12/2016 | Srugo et al. | A63B 24/00 |
| 2017/0165526 | A1* | 6/2017 | Bakun | A63B 24/0075 |
| 2018/0001178 | A1* | 1/2018 | Jafarifesharaki | A63B 71/00 |

OTHER PUBLICATIONS

Garmin, How to Use Garmin Connect; Aug. 17, 2015, pp. 1-11 (Year: 2015).*

Dobkin, Wearable motion sensors to continuously measure real-world physical activities; Dec. 2013; pp. 1-14 (Year: 2013).*

Belle; Apps to track your habits and goals; Jun. 16, 2014; pp. 1-13 (Year: 2014).*

Laterback; 5 Awesome Fitness Apps That Offer Rewards; Feb. 19, 2013; pp. 1-4 (Year: 2013).*

* cited by examiner

| DATE | PROGRAM | DETAILS | EXERCISE TIME | DISTANCE |
|---|---|---|---|---|
| 2016-02-23 | 5km running | DAY 1 OF FIRST WEEK | 29min | 5.1km |
| 2016-02-24 | 5km running | DAY 2 OF SECOND WEEK | 31min | 5.5km |
| ... | ... | ... | | |

| DATE | PROGRAM | DETAILS | EXERCISE TIME | DISTANCE |
|---|---|---|---|---|
| 2016-02-23 | 5km running | DAY 1 OF FIRST WEEK | 29min | 5.1km |
| 2016-02-24 | 5km running | DAY 2 OF SECOND WEEK | 31min | 5.5km |
| ... | ... | ... | | |

ELECTRONIC DEVICE AND METHOD FOR LINKING EXERCISE SCHEDULE THEREOF

CROSS-REFERENCE TO RELATED APPLICATION

This application is based on and claims priority under 35 U.S.C. § 119 to a Korean patent application filed on Dec. 23, 2015 in the Korean Intellectual Property Office and assigned Serial number 10-2015-0184770, the disclosure of which is incorporated by reference herein in its entirety.

TECHNICAL FIELD

The present disclosure relates generally to technologies for linking a schedule associated with exercise between a plurality of devices.

BACKGROUND

With the development of electronic technologies, various types of electronic devices have been developed and distributed. Particularly, recently, the distribution of wearable devices, such as smart watches and smart glasses, which may be worn on their users together with electronic devices such as smartphones and tablet personal computers (PCs) has been expanded.

The above-mentioned electronic devices and wearable devices may provide a variety of functions for health management using sensors embedded therein. Further, the electronic devices and the wearable devices may interwork with each other and may provide health management services.

Since a function of a wearable device is more limited than that of an electronic device such as a smartphone, a user of the electronic device may be requested to carry the electronic device when performing a specific type of an exercise schedule. It may be more inconvenient for the user to carry the electronic device during his or her exercise than the wearable device. Also, since the performance of the wearable device is limited, it is difficult to store or manage various exercise schedules in the wearable device. Also, the user may be requested to operate the electronic device and the wearable device to link the electronic device to the wearable device.

SUMMARY

Example aspects of the present disclosure are provided to address the above-mentioned problems and/or disadvantages and to provide at least the advantages described below. Accordingly, an example aspect of the present disclosure is to provide an electronic device for automatically dividing a stored exercise schedule and automatically synchronizing the divided exercise schedules with an external device and a method therefor.

In accordance with an example aspect of the present disclosure, an electronic device is provided. The electronic device may include a communication circuit configured to perform wireless communication, a memory configured to store an exercise schedule capable of being divided into a plurality of segments, and a processor electrically connected with the communication circuit and the memory. The processor may be configured to send a segment automatically selected based on at least one of a policy defined in the electronic device or attributes of an external device among the plurality of segments included in the exercise schedule to the external device, if the electronic device connects with the external device through the wireless communication and to receive an exercise record collected by the external device from the external device, if the electronic device connects with the external device again through the wireless communication after the wireless communication is disconnected.

In accordance with another example aspect of the present disclosure, a method is provided. The method may include dividing an exercise schedule into a plurality of segments, sending a segment automatically selected based on at least one of a policy defined in the electronic device or attributes of the external device among the plurality of segments to the external device if the electronic device connects with an external device through wireless communication, and receiving an exercise record collected by the external device from the external device, if the electronic device connects with the external device again through wireless communication after the wireless communication is disconnected.

In accordance with another example aspect of the present disclosure, an electronic device is provided. The electronic device may include a communication circuit, a memory configured to store schedule information associated with user activity, and a processor. The processor may be configured to verify attribute information of at least one external electronic device operatively connected with the electronic device, to select part of the schedule information based on the attribute information, and to send the selected part of the schedule information to the at least one external electronic device using the communication circuit.

Other aspects, advantages, and salient features of the disclosure will become apparent to those skilled in the art from the following detailed description, which, taken in conjunction with the annexed drawings, discloses various example embodiments of the present disclosure.

BRIEF DESCRIPTION OF THE DRAWINGS

The above and other aspects, features, and advantages of the present disclosure will be more apparent from the following detailed description, taken in conjunction with the accompanying drawings, in which like reference numerals refer to like elements, and wherein.

Throughout the drawings, it should be noted that like reference numbers are used to depict the same or similar elements, features, and structures.

DETAILED DESCRIPTION

Figure 1:
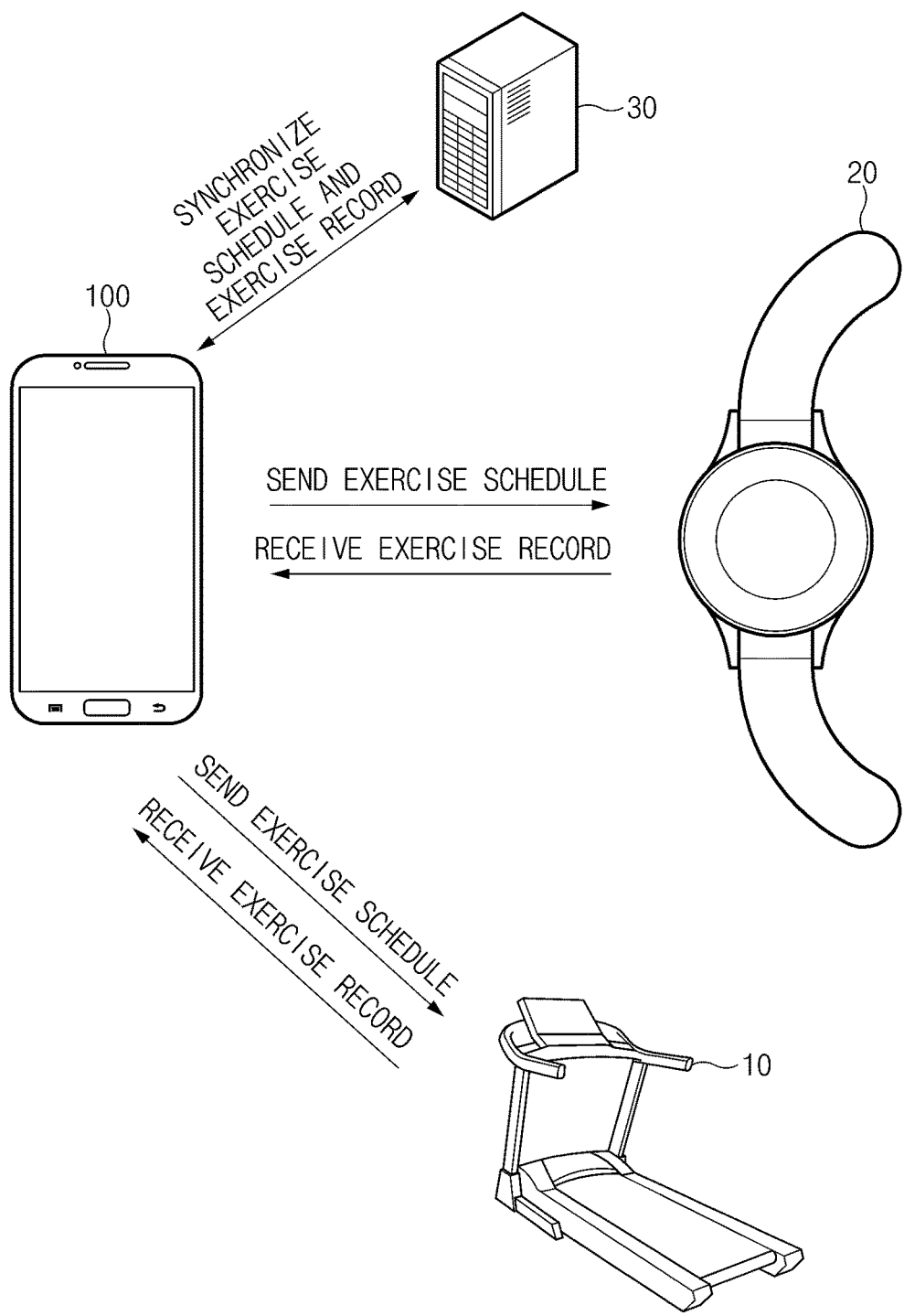
FIG. 1 is a diagram illustrating an example environment where an electronic device operates according to an example embodiment.

Hereinafter, the present disclosure is described with reference to the accompanying drawings. However, the present disclosure is not intended to be limited to the various example embodiments, and it is understood that it should include all modifications and/or, equivalents and alternatives within the scope and technical range of the present disclosure. With respect to the descriptions of the drawings, like reference numerals refer to like elements.

In the disclosure disclosed herein, the expressions "have", "may have", "include" and "comprise", or "may include" and "may comprise" used herein indicate existence of corresponding features (e.g., elements such as numeric values, functions, operations, or components) but do not exclude presence of additional features.

In the disclosure disclosed herein, the expressions "A or B", "at least one of A or/and B", or "one or more of A or/and B", and the like used herein may include any and all combinations of one or more of the associated listed items. For example, the term "A or B", "at least one of A and B", or "at least one of A or B" may refer to all of the case (1) where at least one A is included, the case (2) where at least one B is included, or the case (3) where both of at least one A and at least one B are included.

The expressions such as "1st", "2nd", "first", or "second", and the like used in various embodiments of the present disclosure may refer to various elements irrespective of the order and/or priority of the corresponding elements, but do not limit the corresponding elements. The expressions may be used to distinguish one element from another element. For instance, both "a first user device" and "a second user device" indicate different user devices from each other irrespective of the order and/or priority of the corresponding elements. For example, a first component may be referred to as a second component and vice versa without departing from the scope of the present disclosure.

It will be understood that when an element (e.g., a first element) is referred to as being "(operatively or communicatively) coupled with/to" or "connected to" another element (e.g., a second element), it can be directly coupled with/to or connected to the other element or an intervening element (e.g., a third element) may be present. On the other hand, when an element (e.g., a first element) is referred to as being "directly coupled with/to" or "directly connected to" another element (e.g., a second element), it should be understood that there are no intervening element (e.g., a third element).

Depending on the situation, the expression "configured to" used herein may be used as, for example, the expression "suitable for", "having the capacity to", "designed to", "adapted to", "made to", or "capable of". The term "configured to" must not mean only "specifically designed to" hardwarily. Instead, the expression "a device configured to" may denote that the device is "capable of" operating together with another device or other components. For example, a "processor configured to perform A, B, and C" may refer, for example, to a dedicated processor, various processing circuitry, a generic-purpose processor (e.g., a central processing unit (CPU) or an application processor) which may perform corresponding operations by executing one or more software programs which stores a dedicated processor (e.g., an embedded processor) for performing a corresponding operation.

Terms used in this disclosure are used to describe various example embodiments of the present disclosure and are not intended to limit the scope of the present disclosure. The terms of a singular form may include plural forms unless otherwise specified. Unless otherwise defined herein, all the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal detect unless expressly so defined herein in various embodiments of the present disclosure. In some cases, even if terms are terms which are defined in the disclosure, they should not be interpreted to exclude embodiments of the present disclosure.

Electronic devices according to various embodiments of the present disclosure may include at least one of, for example, smart phones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group (MPEG-1 or MPEG-2) Audio Layer 3 (MP3) players, mobile medical devices, cameras, or wearable devices, or the like, but are not limited thereto. According to various embodiments, the wearable devices may include at least one of accessory-type wearable devices (e.g., watches, rings, bracelets, anklets, necklaces, glasses, contact lenses, or head-mounted-devices (HMDs)), fabric or clothing integral wearable devices (e.g., electronic clothes), body-mounted wearable devices (e.g., skin pads or tattoos), or implantable wearable devices (e.g., implantable circuits), or the like, but is not limited thereto.

In various embodiments, the electronic devices may be smart home appliances. The smart home appliances may include at least one of, for example, televisions (TVs), digital versatile disk (DVD) players, audios, refrigerators, air conditioners, cleaners, ovens, microwave ovens, washing machines, air cleaners, set-top boxes, home automation control panels, security control panels, TV boxes (e.g., Samsung HomeSync™, Apple TV™, or Google TV™), game consoles (e.g., Xbox™ and PlayStation™), electronic dictionaries, electronic keys, camcorders, or electronic picture frames, or the like, but are not limited thereto.

In various embodiments, the electronic devices may include at least one of various medical devices (e.g., various portable medical measurement devices (e.g., blood glucose meters, heart rate meters, blood pressure meters, or thermometers, and the like), a magnetic resonance angiography (MRA), a magnetic resonance imaging (MRI), a computed tomography (CT), scanners, or ultrasonic devices, and the like), navigation devices, global navigation satellite system (GNSS), event data recorders (EDRs), flight data recorders (FDRs), vehicle infotainment devices, electronic equipment for vessels (e.g., navigation systems, gyrocompasses, and the like), avionics, security devices, head units for vehicles, industrial or home robots, automatic teller's machines (ATMs), points of sales (POSs), or internet of things (e.g., light bulbs, various sensors, electric or gas meters, sprinkler devices, fire alarms, thermostats, street lamps, toasters, exercise equipment, hot water tanks, heaters, boilers, and the like), or the like, but are not limited thereto.

According to various embodiments, the electronic devices may include at least one of parts of furniture or buildings/structures, electronic boards, electronic signature receiving devices, projectors, or various measuring instruments (e.g., water meters, electricity meters, gas meters, or wave meters, and the like), or the like, but are not limited thereto. The electronic devices according to various embodiments of the present disclosure may be one or more combinations of the above-mentioned devices. The electronic devices according to various embodiments of the present disclosure may be flexible electronic devices. Also, electronic devices according to various embodiments of the present disclosure are not limited to the above-mentioned devices, and may include new electronic devices according to technology development Hereinafter, electronic devices according to various embodiments will be described with reference to the accompanying drawings. The term "user" used herein may refer to a person who uses an electronic device or may refer to a device (e.g., an artificial electronic device) that uses an electronic device.

FIG. 1 is a diagram illustrating an example environment where an electronic device operates according to an example embodiment.

Referring to FIG. 1, an electronic device 100 according to an example embodiment may communicate with an external device 10, an external device 20, and a server 30. The electronic device 100 may be a mobile terminal, for example, a smartphone or a tablet personal computer (PC), but is not limited thereto. The external device 10 may be fitness equipment, for example, a treadmill, or the like, but is not limited thereto. The external device 20 may be a wearable device, for example, a smart watch, or the like, but is not limited thereto. The server 30 may be a computing device which may receive data, may store the received data, and may send the stored data to the electronic device 100. The server 30 may be, for example, a personal health record (PHR) server 30, or the like, but is not limited thereto.

The electronic device 100 may send an exercise schedule stored in the electronic device 100 to the external device 20. For ease of explanation, reference will be made herein to external device 20. However, it should be understood that the description applies equally to external device 10. The exercise schedule may be data including an exercise plan for each date provided from an exercise application installed in the electronic device 100. The electronic device 100 may divide an exercise schedule, for example, for each date. The electronic device 100 may automatically select an exercise schedule corresponding to, for example, a current time among the divided exercise schedules. The electronic device 100 may automatically send the selected exercise schedule to the external device 20 at a specified time. The external device 20 may receive the exercise schedule from the electronic device 100. The external device 20 may verify integrity of the received exercise schedule based on a field included in the received exercise schedule and magnitude of a field value. After being disconnected from the electronic device 100, the external device 20 may detect exercise of it user using a global positioning system (GPS) module, a sensor, or the like included in the external device 20. The external device 20 may generate an exercise record including information, such as a movement distance, a speed, or a time, using the detected data. After the exercise of the user is ended, if connected with the electronic device 100, the external device 20 may send the exercise record to the electronic device 100. After the external device 20 receives the exercise schedule, if the user does not perform exercise during a specified time, the external device 20 may provide notification or reward details expected upon performing the exercise.

The electronic device 100 may receive the exercise record from the external device 20. The electronic device 100 may store the received exercise record and may display the exercise record on its display. The electronic device 100 may link the exercise schedule to the exercise record to display the linked exercise schedule and exercise record. The electronic device 100 may update progress of the exercise schedule using the exercise record. The electronic device 100 may send the exercise schedule, the progress of the exercise schedule or the exercise record to the server 30. If the exercise schedule, the progress of the exercise schedule or the exercise record is damaged or deleted, the electronic device 100 may receive an exercise schedule, progress of the exercise schedule or an exercise record from the server 30.

Detailed contents for the electronic device 100 and the external device 20 may be applied to the external device 10 in the same manner.

Figure 2:
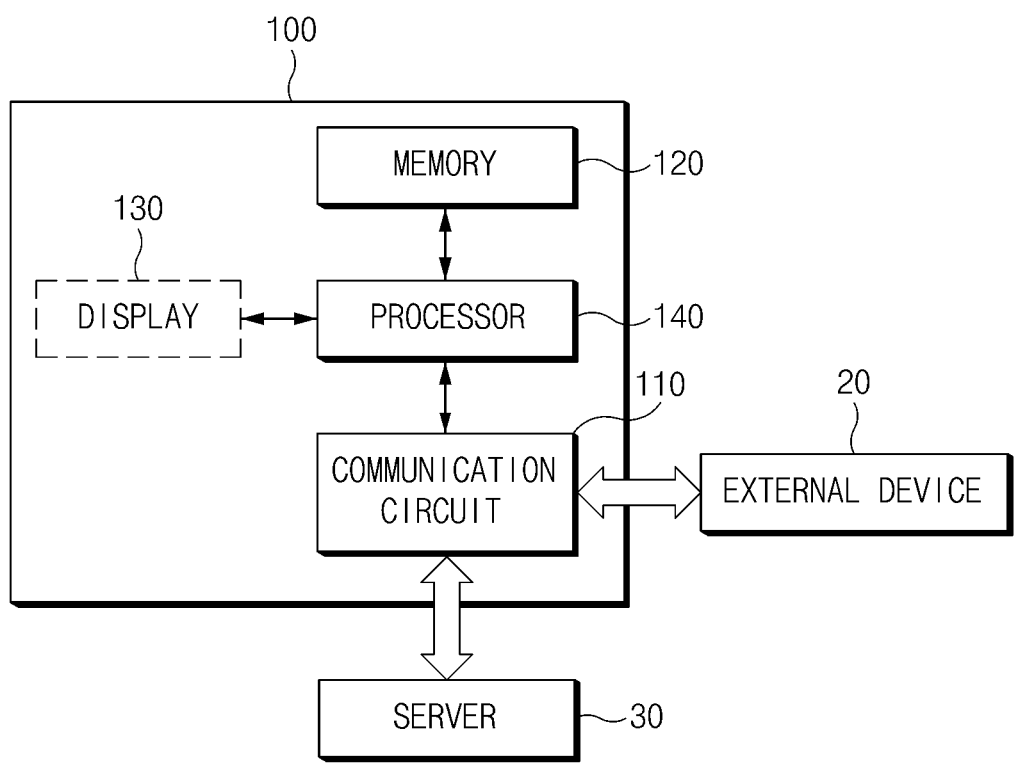
FIG. 2 is a block diagram illustrating an example configuration of an electronic device according to an example embodiment.

FIG. 2 is a block diagram illustrating an example configuration of an electronic device according to an example embodiment.

Referring to FIG. 2, an electronic device 100 according to an embodiment may include a communication circuit 110, a memory 120, a display 130, and a processor 140.

The communication circuit 110 may include various communication circuitry configured to perform wireless communication. The communication circuit 110 may perform wireless communication using a communication mode, for example, Bluetooth low energy (BLE) or Wireless-Fidelity (Wi-Fi) direct. The communication circuit 110 may perform communication using a transport protocol, for example, an advanced and adaptive network technology plus (ANT+) protocol or a session announcement protocol (SAP). The communication circuit 110 may communicate with an external device 20 and a server 30. The communication circuit 110 may perform communication with the external device 20 and the server 30 in different ways. For example, the communication circuit 110 may communicate with the external device 20 in a BLE mode and may communicate with the server 30 in a long term evolution (LTE) mode.

The memory 120 may store an exercise schedule (or schedule information) associated with user activity. The exercise schedule stored in the memory 120 may be divided into a plurality of segments. The exercise schedule may include, a component, such as an exercise time or distance, and an execution plan for each date. The memory 120 may store an exercise record associated with the exercise schedule.

The display 130 may display the exercise schedule or the exercise record. The display 130 may display progress of the exercise schedule. The display 130 may display a message for informing a user of the electronic device 100 that exercise is not performed and may display reword details associated with the exercise schedule or the exercise record.

The processor 140 may include various processing circuitry and be electrically connected with the communication circuit 110, the memory 120, and the display 130. The processor 140 may control the communication circuit 110, the memory 120, and the display 130.

If the electronic device 100 connects with the external device 20 through, for example, wireless communication, the processor 140 may send a segment automatically selected based on at least one of a policy defined in the electronic device 100 or attributes of the external device 20 among the plurality of segments included in the exercise schedule to the external device 20.

According to an embodiment, the processor 140 may divide the exercise schedule into the plurality of segments based on the at least one of the policy defined in the electronic device 100 or the attributes of the external device 20. The policy may be an exercise schedule management policy for guiding the user to perform an optimum exercise program at the right time. The policy may be criteria of dividing the exercise schedule and may be configured such that, for example, capacity, a date, or a type of exercise is the criteria of dividing the exercise schedule. The attributes information may include, for example, at least part of a type, a category, a model name, or capacity, associated with the external device 20. For example, if the external device 20 is a wearable device, the type may be information about a type (e.g., a watch type, a clip type, or the like) of the wearable device. The category may be, for example, information about a function (e.g., a display function, a vibration function, a voice function, a text-to-speech (TTS) function, or the like) supported by the wearable device. The model name may be, for example, information about a model name of the wearable device. The capacity may be, for example, information about capacity (e.g., memory capacity, battery capacity, network band capacity, or the like) in which the wearable device may receive data. The processor 140 may verify the policy defined in the electronic device 100 and the attributes of the external device 20. The processor 140 may verify the policy and the attributes of the external device 20 and may divide the exercise schedule into the plurality of segments based on capacity, a date, or a type of exercise. Hereinafter, an embodiment of dividing the exercise schedule will be described in greater detail below with reference to FIG. 3.

According to an embodiment, the processor 140 may select some of the plurality of segments (or part (e.g., a subset) of schedule information) based on the policy defined in the electronic device 100 or information about the attributes of the external device 20. The processor 140 may select, for example, all of an exercise schedule which is being currently performed or is expected to be performed or part of an exercise schedule which should be performed in the day. Hereinafter, an embodiment of selecting the exercise schedule will be described in greater detail below with reference to FIG. 3.

According to an embodiment, the processor 140 may select a portion mapped to the attributes information of the external device 20 in schedule information. For example, if the attributes information corresponds to first attributes information, the processor 140 may select a first part of the schedule information. If the attributes information corresponds to second attributes information, the processor 140 may select a second part of the schedule information. For example, the electronic device 100 may determine a type of a device connected with the electronic device 100 using attributes information received from the external device 20. For example, if the type of the connected device is determined as a treadmill based on the received attributes information, the electronic device 100 may select a segment associated with the treadmill among the plurality of segments.

According to an embodiment, the processor 140 may select part of the schedule information further based on context information of the user. The context information may include, for example, information associated with a state where the electronic device 100 connects with the external device 20, the last connection time, progress of a schedule, a physical condition of the user, or an environment around the electronic device 100. For example, the processor 140 may verify the physical condition of the user using a biometric sensor (e.g., a biometric sensor 1240I of FIG. 12). The processor 140 may select, for example, some of a plurality of schedule information based on biometric information (e.g., a temperature, a pulse, blood pressure, or the like) of the user. For another example, the processor 140 may select part of the schedule information based on an environment (e.g., a temperature, humidity, and concentrations of find dust) around the electronic device 100. The processor 140 may sense, for example, an environment around the electronic device 100 using a sensor (e.g., a temperature/humidity sensor 1204K of FIG. 12) and may select some of the plurality of schedule information using the sensed sensor data. For another example, if a state where the electronic device 100 connects with the external device 20 is good, the processor 140 may select much schedule information than if the connection state is bad. For another example, if the user does not perform exercise corresponding to an exercise schedule during a specified time, the processor 140 may select a previously sent exercise schedule again.

According to an embodiment, the processor 140 may send the selected segment (or part of schedule information) to the external device 20 using the communication circuit 110. The processor 140 may send the selected segment to the external device 20 through wireless communication. The processor 140 may automatically send the selected segment to the external device 20 based on a policy associated with transmission, defined in the electronic device 100. For example, the processor 140 may automatically send the selected segment to the external device 20 at intervals of a specified time. For example, if receiving information for providing notification that a segment is completed, sent from the external device 20, the processor 140 may send the selected segment to the external device 20. The processor 140 may link an exercise schedule without an operation of the user by automatically sending an exercise schedule to the external device 20 at a specified time.

According to an embodiment, the processor 140 may convert the selected segment into a designated structure to secure integrity for the selected segment and may send the converted segment to the external device 20. For example, the processor 140 may convert the selected segment into an extensible markup language (XML) document. The XML document may include a specified field (e.g., a field associated with an exercise event and an exercise time or distance). The processor 140 may send the converted segment to the external device 20 using the communication circuit 110. The external device 20 may receive the converted segment and may determine integrity of the segment. To determine the integrity, for example, the external device 20 may determine whether the received segment includes all of specified fields and whether a field value included in each of fields is included in a specified range. As described above, the external device 20 may easily determine integrity for an exercise schedule by converting the exercise schedule into a designated structure and sending the converted exercise schedule to the electronic device 100.

After the wireless communication is disconnected, if the electronic device 100 connects with the external device 20 again through the wireless communication, the processor 140 may receive exercise records collected by the external device 20 from the external device 20. After the selected segment is sent, communication between the electronic device 100 and the external device 20 may be disconnected. The user carries the external device 20 and may perform exercise. The external device 20 may detect movement of the user and may collect an exercise record. After the exercise is ended, the electronic device 100 may connect with the external device 20 again through the wireless communication. If connected with the electronic device 100, the external device 20 may send an exercise record collected while being disconnected from the electronic device 100 to the electronic device 100. Alternatively, if the electronic device 100 connects with the external device 20 again, the processor 140 may request the external device 20 to send the exercise record collected while disconnected from the external device 20. The processor 140 may receive the exercise record collected by the external device 20 from the external device 20 using the communication circuit 110. A communication mode used while the exercise schedule is sent may be different from a communication mode used while the exercise record is received.

According to an embodiment, the processor 140 may update progress of an exercise schedule based on the exercise record. If receiving the exercise record from the external device 20 (e.g., a wearable device or fitness equipment), the processor 140 may determine whether exercise is performed based on the exercise schedule. The processor 140 may update progress of the exercise schedule by matching and storing the exercise record with the exercise schedule.

According to an embodiment, the processor 140 may display the exercise record or the progress of the exercise schedule on the display 130. The processor 140 may display a list of exercise records on the display 130. For example, the processor 140 may arrange and display exercise records associated with one exercise schedule on the display 140 in a specified order (e.g., according to a date, the external device 20 which collects the exercise records, an exercise event, or the like). The processor 140 may display an exercise schedule on the display 130 to ascertain progress of the exercise schedule. For example, the processor 140 may display an exercise schedule which is not performed and an exercise schedule performed, using different attributes (e.g., a color and a size). For example, the processor 140 may display the exercise schedule which is not performed using a blue color and may display the exercise schedule performed using a black color.

According to an embodiment, the processor 140 may display reward associated with an exercise record or an exercise schedule. The processor 140 may display a pop-up window of displaying reward including an accumulated amount of exercise, an exercise effect, or the like associated with performed exercise on the display 130. After sending an exercise schedule to the external device 20, if an exercise record is not received during a specified time, the processor 140 may reward on the display 130. In this case, the processor 140 may display reward expected to perform exercise based on an exercise schedule on the display 130.

According to an embodiment, the processor 140 may send an exercise record or progress of an exercise schedule to the server 30 using the communication circuit 110. If the exercise record or the progress of the exercise schedule is changed, the processor 140 may synchronize the exercise record or the progress of the exercise schedule with the server 30. The processor 140 may receive an exercise record or an exercise schedule stored in the server 30 from the server 30.

The external device 20 may include a communication circuit (not shown), a memory (not shown), a display (not shown), and a processor (not shown). The external device 20 may be a wearable device such as a smart watch or fitness equipment such as a treadmill. The external device 20 may receive all or part of an exercise schedule from the electronic device 100 using the communication circuit, may check integrity of the received exercise schedule, and display the received exercise schedule on the display. If the user performs exercise, the external device 20 may collect an exercise record. The external device 20 may send the collected exercise record to the electronic device 100.

The server 30 may include a communication circuit (not shown), a memory (not shown), and a processor (not shown). The server 30 may receive user activity information (e.g., an exercise schedule, progress of the exercise schedule, and/or an exercise record) from the electronic device 100 and may store the received data. The server 30 may send the exercise schedule, the progress of the exercise schedule and/or the exercise record to the electronic device 100.

According to an embodiment, an electronic device may include a communication circuit configured to perform wireless communication, a memory configured to store an exercise schedule divided into a plurality of segments, and a processor configured to electrically connect with the communication circuit and the memory. The processor may be configured to send a segment automatically selected based on at least one of a policy defined in the electronic device or attributes of an external device in the exercise schedule to the external device if the electronic device connects with the external device through the wireless communication and receive an exercise record collected by the external device from the external device if the electronic device connects with the external device again through the wireless communication after the wireless communication is disconnected.

According to an embodiment, the processor may be configured to divide the exercise schedule into the plurality of segments based on the at least one of the policy defined in the electronic device or the attributes of the external device.

According to an embodiment, the processor may be configured to divide the exercise schedule into the plurality of segments based on capacity, a date, or a type of exercise.

According to an embodiment, the processor may be configured to convert the selected segment into a designated structure to secure integrity for the selected segment and send the converted segment to the external device.

According to an embodiment, the processor may be configured to automatically send the selected segment to the external device at intervals of a specified time.

According to an embodiment, the processor may be configured to compare the exercise record with the exercise schedule if receiving the exercise record from the external device and update progress of a portion with the highest similarity to the exercise record in the exercise record.

According to an embodiment, the processor may be configured to update progress of the exercise schedule based on the exercise record.

According to an embodiment, the electronic device may further include a display electrically connected with the processor. The processor may be configured to display the exercise record or the progress of the exercise schedule on the display.

According to an embodiment, the electronic device may further include a display electrically connected with the processor. The processor may be configured to display reward associated with the exercise record or the exercise schedule on the display.

According to an embodiment, the communication circuit may be configured to perform wireless communicate with a plurality of external devices including a first external device and a second external device. The processor may be configured to update the progress of the exercise schedule based on a first exercise record if receiving the first exercise record from the first external device, send the first exercise record to the second external device using the communication circuit, update the progress of the exercise schedule based on a second exercise record if receiving the second exercise record from the second external device, and send the second exercise record to the first external device using the communication circuit.

According to an embodiment, the electronic device may further include a display electrically connected with the processor. The communication circuit may be configured to perform wireless communication with a plurality of external devices. The processor may be configured to display the exercise record or the progress of the exercise schedule on the display to identify an external device which sends the exercise record among the plurality of external devices.

According to an embodiment, the processor may be configured to send the exercise record or the progress of the exercise schedule to a server using the communication circuit.

According to an embodiment, the processor may be configured to receive an exercise schedule from a server using the communication circuit if the exercise schedule is deleted.

According to an embodiment, an electronic device may include a communication circuit, a memory configured to store schedule information associated with user activity, and a processor. The processor may be configured to verify attributes information of at least one external electronic device operatively connected with the electronic device, select part (e.g., a subset) of schedule information based on the at least attributes information, and send the part of the schedule information to the at least one external device using the communication circuit.

According to an embodiment, the attributes information may include at least part of a type, a category, a model name, or capacity, associated with the at least one external electronic device.

According to an embodiment, the processor may be configured to select the part of the schedule information further based on context information of a user of the electronic device.

According to an embodiment, the processor may be configured to select a first part of the schedule information if the attributes information corresponds to first attributes information and select a second part of the schedule information if the attributes information corresponds to second attributes information.

According to an embodiment, the at least one external electronic device may include a first external electronic device and a second external electronic device. The processor may be configured to obtain first information associated with user activity from the first external electronic device, obtain second information associated with user activity from the second external electronic device, and provide at least part of the first information or the second information using a display operatively connected with the electronic device.

Figure 3:
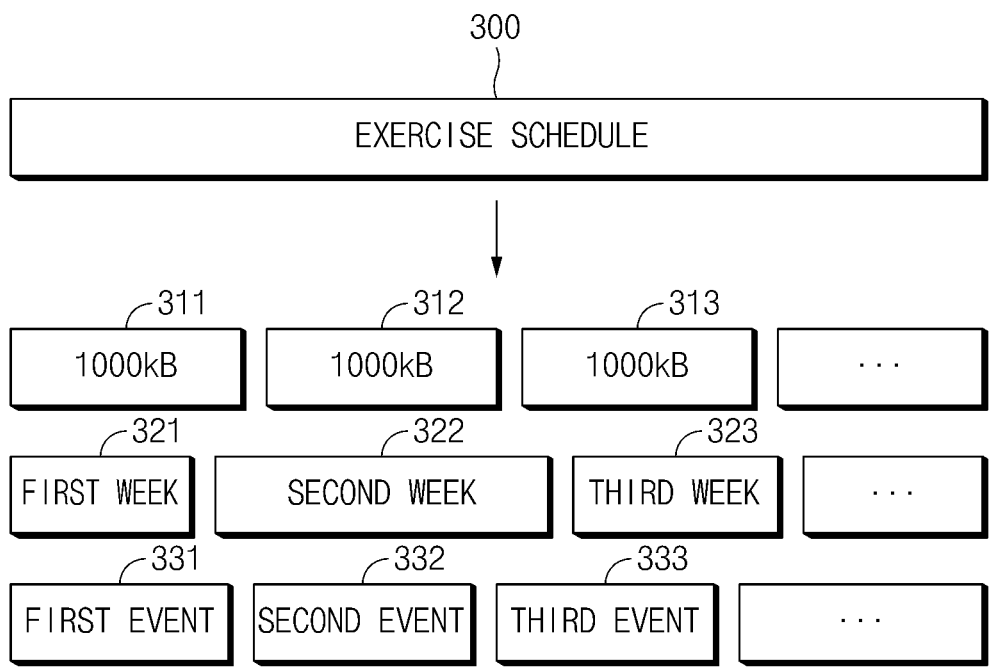
FIG. 3 is a diagram illustrating an example implementation of dividing an exercise schedule at an electronic device according to an example embodiment.

FIG. 3 is a diagram illustrating an example implementation of dividing an exercise schedule at an electronic device according to an example embodiment.

According to an embodiment, an electronic device (e.g., a processor 140 of FIG. 2) may divide an exercise schedule into a plurality of segments based on at least one of a policy defined in the electronic device or attributes of an external device.

Referring to FIG. 3, an exercise schedule 300 may be divided into a plurality of segments 311, 312, 313, 321, 322, 323, 331, 332, and 333 based on capacity, a date, or a type of exercise.

According to an embodiment, the exercise schedule 300 may be divided into a plurality of segments 311, 312, and 313, each of which has specified capacity. For example, the exercise schedule 300 may be divided into the first segment 311, the second segment 312, the third segment 313, and the like in units of 1000 kilobytes. The first segment 311, the second segment 312, and the third segment 313 may be sequentially sent to an external device (e.g., an external device 20 of FIG. 2). Part of the first segment 311, the second segment 312, and the third segment 313 may be sent to the external device based on capacity of the external device. As the exercise schedule 300 is divided based on the specified capacity, it may be quickly sent to the external device. The first segment 311, the second segment 312, and the third segment 313 may differ in size according to the capacity of the external device. For example, if the capacity of the external device is higher, the exercise schedule 300 may be divided into larger units. If the capacity of the external device is lower, the exercise schedule 300 may be divided into smaller units.

According to an embodiment, the exercise schedule 300 may be divided into the plurality of segments 321, 322, and 323 based on a date when the exercise schedule 300 is performed. For example, the exercise schedule 300 may be divided into the first segment 321 including an exercise schedule for a first week, the second segment 322 including an exercise schedule for a second week, and the third segment 323 including an exercise schedule for a third week. A segment corresponding to a current date among the first segment 321, the second segment 322, and the third segment 323 may be sent to the external device. For example, as eight days pass after the exercise schedule 300 is started, the second segment 322 may be sent to the external device. As shown in FIG. 3, an embodiment is exemplified as the exercise schedule 300 may be divided on a weekly basis. Embodiments are not limited thereto. For example, the exercise schedule 300 may be divided on a daily basis or on a monthly basis.

According to an embodiment, the exercise schedule 300 may be divided into the plurality of segments 331, 332, and 333 based on its type. For example, the exercise schedule 300 may be divided into the first segment 331 including the exercise schedule associated with a first event (e.g., running), the second segment 332 including the exercise schedule associated with a second event (e.g., swimming), and the third segment 333 including the exercise schedule associated with a third event (e.g., cycling). The first segment 331, the second segment 332, and the third segment 33 may be sequentially sent to the external device. The first segment 331, the second segment 332, and the third segment 33 may be sent to the external device in a specified priority order (e.g., event preference of a user of the electronic device). For example, the processor 140 may send the first segment 331, the second segment 332, and the third segment 333 to the external device 20 based on a type of the external device 20. For example, if recognizing the external device 20 as a treadmill, the processor 140 may send a segment (e.g., the first segment 331) associated with the treadmill to the external device 20.

Figure 4:
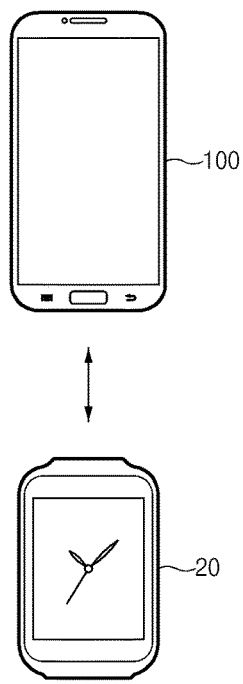
FIG. 4 is a diagram illustrating an example implementation of sending an exercise schedule to an external device at an electronic device according to an example embodiment.

FIG. 4 is a diagram illustrating an example implementation of sending an exercise schedule to an external device at an electronic device according to an example embodiment.

Referring to FIG. 4, an electronic device 100 may interwork with an external device 20. The electronic device 100 may receive an exercise record from the external device 20. The external device 20 may store an exercise record including information about a date when data are collected, a program name, schedule detailed information, an exercise time, and a distance.

For example, the electronic device 100 may send an exercise schedule on day 1 of a first week for 5 km running on Feb. 23, 2016 to the external device 20. The external device 20 may collect an exercise record corresponding to the received exercise schedule. The external device 20 may collect an exercise record including an exercise time of 29 minutes and a distance of 5.1 km. If exercise is ended, the external device 20 may send the exercise record to the electronic device 100. The electronic device 100 may store the received exercise record.

For another example, the electronic device 100 may send an exercise schedule on day 2 of the first week for the 5 km running on Feb. 24, 2016 to the external device 20. The external device 20 may collect an exercise record corresponding to the received exercise schedule. The external device 20 may collect, for example, an exercise record including an exercise time of 31 minutes and a distance of 5.5 km. If exercise is ended, the external device 20 may send the exercise record to the electronic device 100. The electronic device 100 may store the received exercise record.

Figure 5:
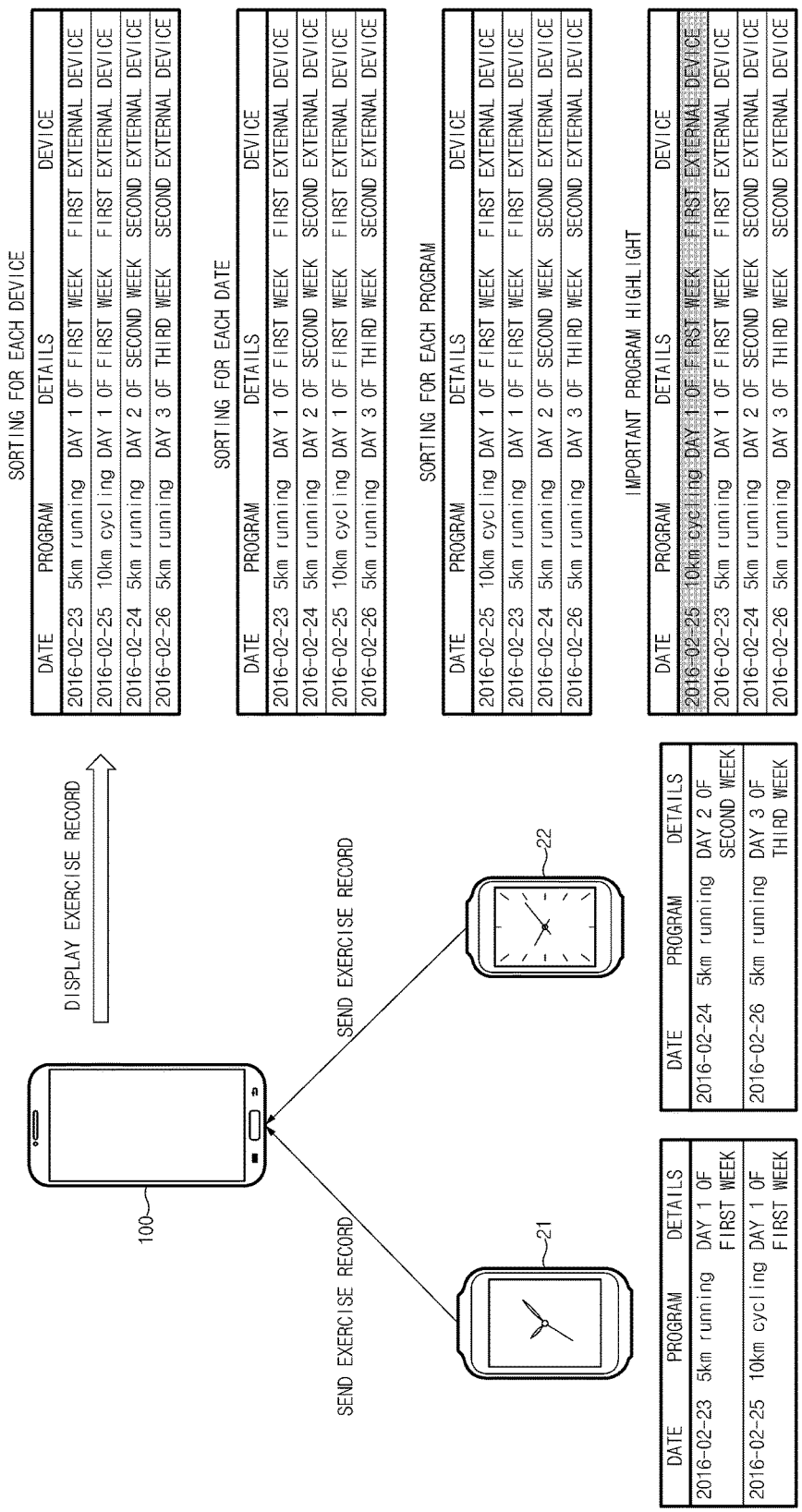
FIG. 5 is a diagram illustrating an example implementation of displaying exercise records received from a plurality of external devices at an electronic device according to an example embodiment.

FIG. 5 is a diagram illustrating an example implementation of displaying exercise records received from a plurality of external devices at an electronic device according to an example embodiment.

According to an embodiment, an electronic device 100 (e.g., a processor 140 of FIG. 2) may perform wireless communication with a plurality of external devices including a first external device 21 and a second external device 22 using a communication circuit 110 of FIG. 2. If receiving a first exercise record (or first information) associated with user activity from the first external device 21, the electronic device 100 (e.g., the processor 140) may update progress of an exercise schedule based on the first exercise record. If receiving a second exercise record (or second information) associated with user activity from the second external device 22, the electronic device 100 may update progress of an exercise schedule based on the second exercise record. The electronic device 100 may display an exercise record or progress of an exercise schedule on its display to identify an external device which sends the exercise record among the plurality of external devices.

Referring to FIG. 5, the electronic device 100 according to an embodiment may communicate with the first external device 21 and the second external device 22.

The electronic device 100 may send an exercise schedule to the first external device 21 and may receive an exercise record corresponding to the sent exercise schedule from the first external device 21. For example, the electronic device 100 may send an exercise schedule on day 1 of a first week for 5 km running on Feb. 23, 2016 to the first external device 21. The electronic device 100 may receive an exercise record corresponding to the corresponding exercise schedule from the first external device 21. The electronic device 100 may send an exercise schedule on day 1 of a first week for 10 km cycling on Feb. 25, 2016 to the first external device 21. The electronic device 100 may receive an exercise record corresponding to the corresponding exercise schedule from the first external device 21. The electronic device 100 may allow the first external device 21 and the second external device 22 to share the exercise record with each other by sending the exercise record, received from the first external device 21, to the second external device 22.

The electronic device 100 may send an exercise schedule to the second external device 22 and may receive an exercise record corresponding to the sent exercise schedule from the second external device 22. For example, the electronic device 100 may send an exercise schedule on day 2 of the first week for the 5 km running on Feb. 24, 2016 to the second external device 22. The electronic device 100 may receive an exercise record corresponding to the corresponding exercise schedule from the second external device 22. The electronic device 100 may send an exercise schedule on day 3 of the first week for the 5 km running on Feb. 26, 2016 to the second external device 22. The electronic device 100 may receive an exercise record corresponding to the corresponding exercise schedule from the second external device 22. The electronic device 100 may allow the first external device 21 and the second external device 22 to share the exercise record with each other by sending the exercise record, received from the second external device 22, to the first external device 21.

The electronic device 100 may display the exercise record received from each of the first external device 21 and the second external device 22 on the display. If receiving the exercise record from the first external device 21 or the second external device 22, the electronic device 100 may store information, about a device which sends the exercise record, together with the exercise record. The electronic device 100 may sort and display exercise records with reference to the first external device 21 or the second external device 22 which sends the exercise record. The electronic device 100 may sort and display exercise records in an order of dates when the exercise records are collected. The electronic device 100 may sort and display exercise records with respect to a type of a program (or an exercise event). The electronic device 100 may highlight an important program. For example, if 10 km cycling is an important program, the electronic device 100 may highlight an exercise record associated with the 10 km cycling.

Figure 6:
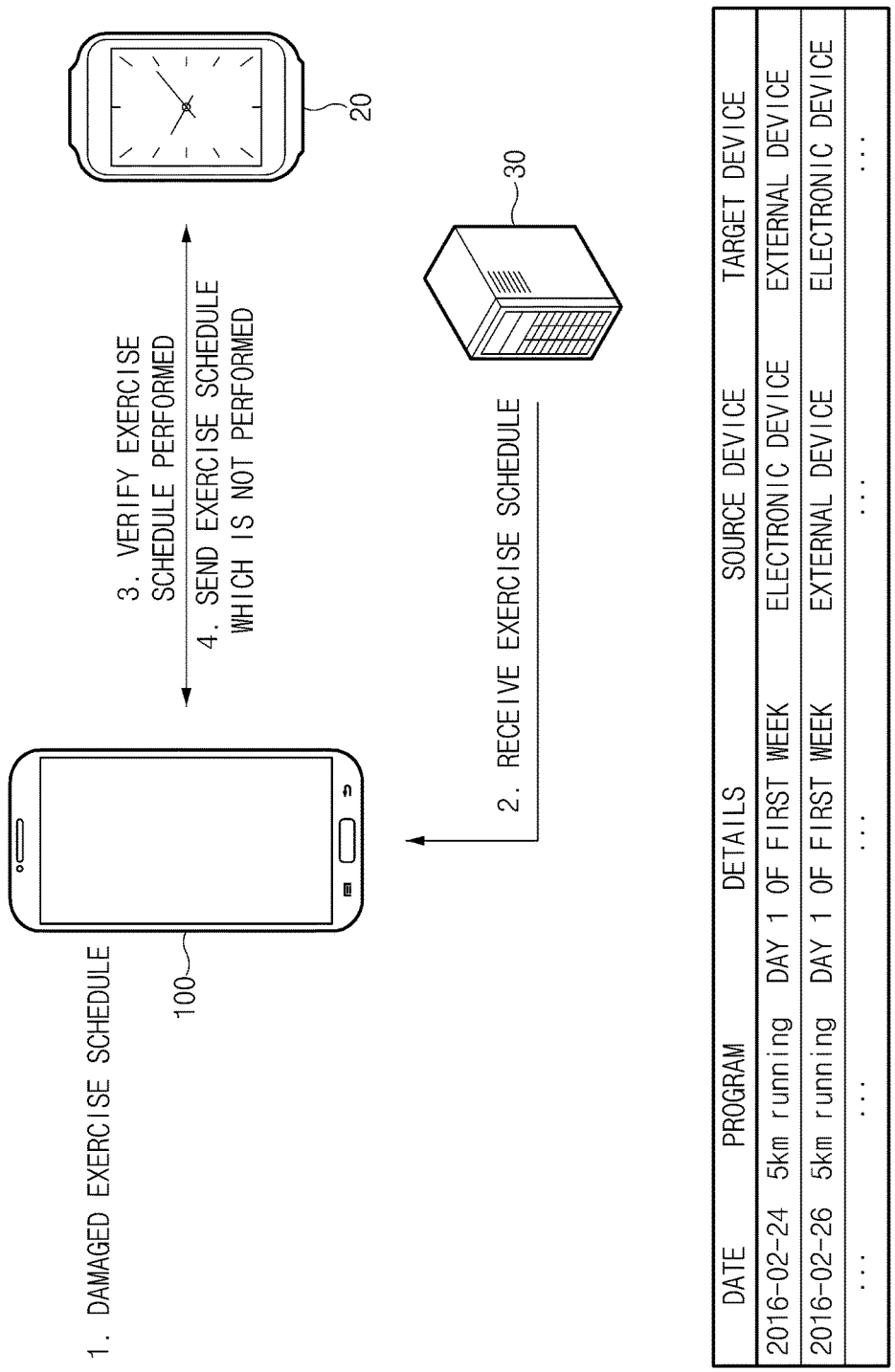
FIG. 6 is a diagram illustrating an example implementation of receiving an exercise schedule from a server at an electronic device according to an example embodiment.

FIG. 6 is a diagram illustrating an example implementation of receiving an exercise schedule from a server at an electronic device according to an example embodiment.

Referring to FIG. 6, an electronic device 100 according to an embodiment may interwork with an external device 20 and a server 30. If transmitting an exercise schedule, if receiving an exercise record, or if updating progress of the exercise schedule, the electronic device 100 may send the exercise schedule, the exercise record, or the progress of the exercise schedule to the server 30. An exercise schedule, an exercise record, or progress of the exercise schedule stored in the electronic device 100, may be synchronized with an exercise schedule, an exercise record, or progress of the exercise schedule stored in the server 30. For example, the server 30 may store an exercise schedule on day 1 of a first week for 5 km running, sent on Feb. 24, 2016 from the electronic device 100 to the external device 20. For another example, the server 30 may store the exercise schedule on day 1 of the first week for the 5 km running, sent on Feb. 26, 2016 from the external device 20 to the electronic device 100.

Data about the exercise schedule, the exercise record, or the progress of the exercise schedule stored in the electronic device 100, may be damaged or deleted (see reference numeral 1). In this case, the electronic device 100 may receive damaged data among the data for the exercise schedule, the exercise record, or the progress of the exercise schedule from the server 30 (see reference numeral 2).

The electronic device 100 may verify an exercise schedule performed before the data are damaged or deleted (see reference numeral 3). For example, the electronic device 100 may verify an exercise schedule or an exercise record stored in the external device 20 to verify an exercise schedule performed. For example, if the exercise schedule on day 1 of the first week for the 5 km running is stored in the external device 20, the electronic device 100 may determine that the exercise schedule on day 1 of the first week for the 5 km running is performed.

The electronic device 100 may send an exercise schedule which is not performed before the data are damaged or deleted to the external device 20 (see reference numeral 4). For example, if determining that the exercise schedule on day 1 of the first week for the 5 km running is performed, the electronic device 100 may send an exercise schedule on day 2 of the first week for the 5 km running to the external device 20.

As described above, although data associated with an exercise schedule or an exercise record is damaged or deleted, the electronic device 100 may receive the corresponding data, may verify an exercise schedule performed, and may send an exercise schedule which is not performed to the external device 20. Thus, exercise according to the exercise schedule may be continuously performed. Also, the electronic device 100 may effectively manage an exercise schedule of a user who uses various wearable devices by updating progress of the exercise schedule using an exercise record received from the external device 20.

Figure 7:
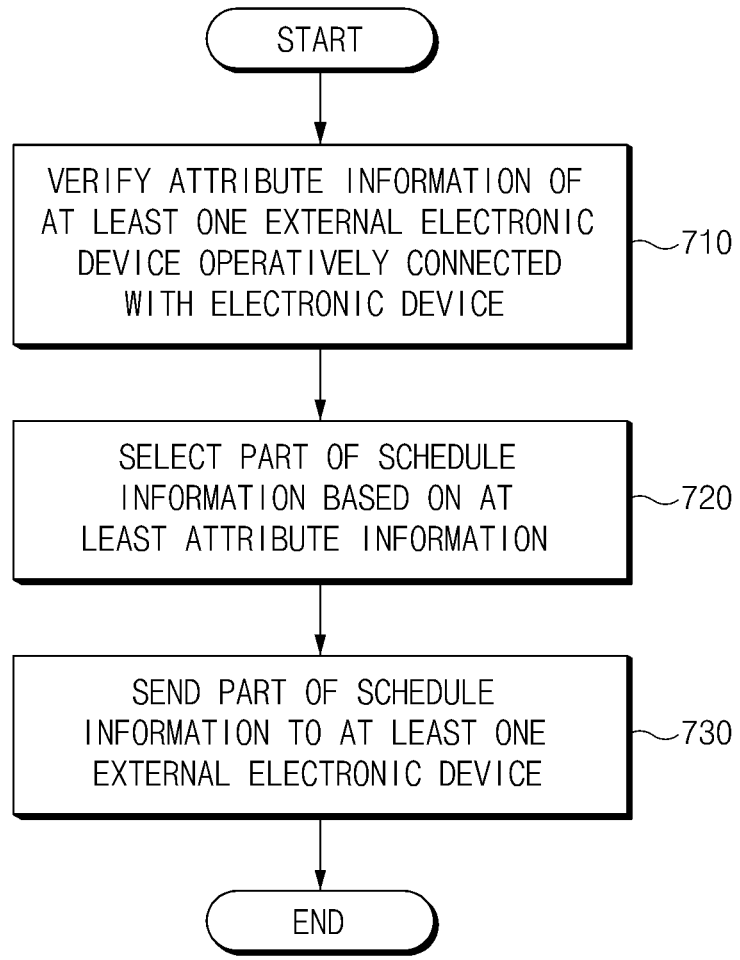
FIG. 7 is a flowchart illustrating an example method for linking an exercise method in an electronic device according to an example embodiment.

FIG. 7 is a flowchart illustrating an example method for linking an exercise method in an electronic device according to an example embodiment.

Operations illustrated in FIG. 7 may include operations processed by an electronic device 100 illustrated in FIGS. 1 and 2. Thus, although there are contents omitted below, contents described about the electronic device 100 with reference to FIGS. 1 and 2 may be applied to the operations illustrated in FIG. 7.

Referring to FIG. 7, in operation 710, the electronic device 100 (e.g., a processor 140 of FIG. 2) may verify attribute information of at least one external electronic device operatively connected with the electronic device 100. The electronic device 100 may wirelessly communicate with the external electronic device. The electronic device 100 may verify attribute information including, for example, information about a type, a category, a model name, capacity, or the like associated with the external electronic device. For example, the electronic device 100 may verify remaining storage capacity of the external electronic device.

In operation 720, the electronic device 100 (e.g., the processor 140) may select part of schedule information based on at least the attribute information. The electronic device 100 may divide the schedule information based on the attribute information and may select part of the divided schedule information. For example, if the remaining storage capacity of the external electronic device is 1000 kilobytes, the electronic device 100 may divide the schedule information in units of 1000 kilobytes. The electronic device 100 may select schedule information which is not sent to the external electronic device among the schedule information divided in units of 1000 kilobytes.

In operation 730, the electronic device 100 (e.g., the processor 140) may send the part of the schedule information to the at least one external electronic device. The electronic device 100 may send the selected part of the schedule information to the external electronic device through wireless communication.

Figure 8:
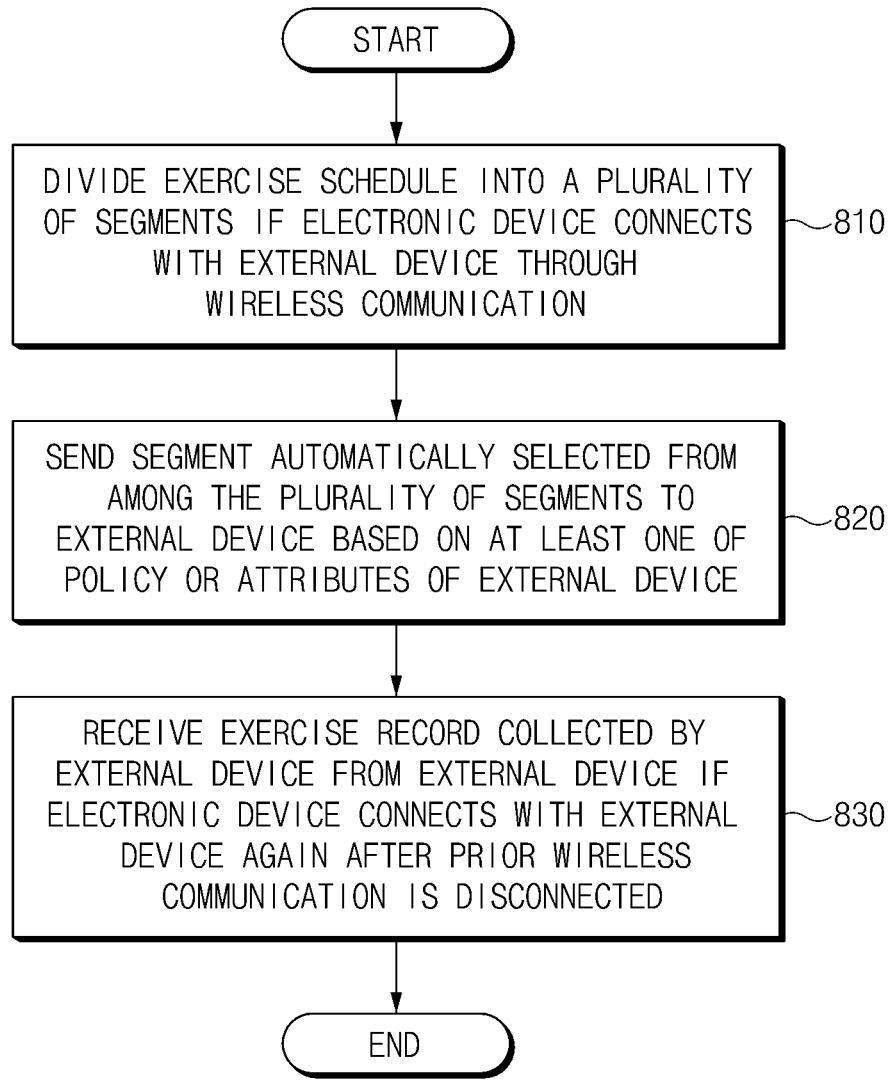
FIG. 8 is a flowchart illustrating an example method for linking an exercise method in an electronic device according to an example embodiment.

FIG. 8 is a flowchart illustrating an example method for linking an exercise method in an electronic device according to an example embodiment.

Operations illustrated in FIG. 8 may include operations processed by an electronic device 100 illustrated in FIGS. 1 and 2. Thus, although there are contents omitted below, contents described about the electronic device 100 with reference to FIGS. 1 and 2 may be applied to the operations shown in FIG. 8.

Referring to FIG. 8, in operation 810, if connected with an external device through wireless communication, the electronic device 100 (e.g., a processor 140 of FIG. 2) may divide an exercise schedule into a plurality of segments. The electronic device 100 may recognize the external device connected with the electronic device 100. The electronic device 100 may divide the exercise schedule in response to a connection with a specified external device. The electronic device 100 may divide the exercise schedule based on a policy defined in the electronic device 100 or attributes of the external device. For example, if the policy is configured to divide the exercise schedule relative to date, the electronic device 100 may divide the exercise schedule for each date.

In operation 820, the electronic device 100 (e.g., the processor 140) may send a segment automatically selected from among the plurality of segments to the external device based on the policy or the attributes of the external device. The electronic device 100 may select all or some of the plurality of segments based on the policy or the attributes of the external device. If the exercise schedule is divided for each date, the electronic device 100 may select a segment corresponding to a current date among the plurality of segments. For example, if initially transmitting the exercise schedule, the electronic device 100 may automatically select a segment including an exercise schedule on day 1 among the plurality of segments. For another example, if the exercise schedule on day 1 is performed, the electronic device 100 may automatically select a segment including an exercise schedule on day 2 among the plurality of segments. The electronic device 100 may send the selected segment to the external device through wireless communication.

In operation 830, if the electronic device 100 (e.g., the processor 140) connects with the external device again through the wireless communication after the prior wireless communication is disconnected, the electronic device 100 may receive an exercise record collected by the external device from the external device. If sending the selected segment to the external device, the electronic device 100 may disconnect from the external device. The external device may collect an exercise record in a state where it disconnects from the electronic device 100. If connected with the external device again, the electronic device 100 may receive an exercise record through the wireless communication from the external device. The exercise record received from the external device may be an exercise record corresponding to the exercise record sent from the electronic device 100.

Figure 9:
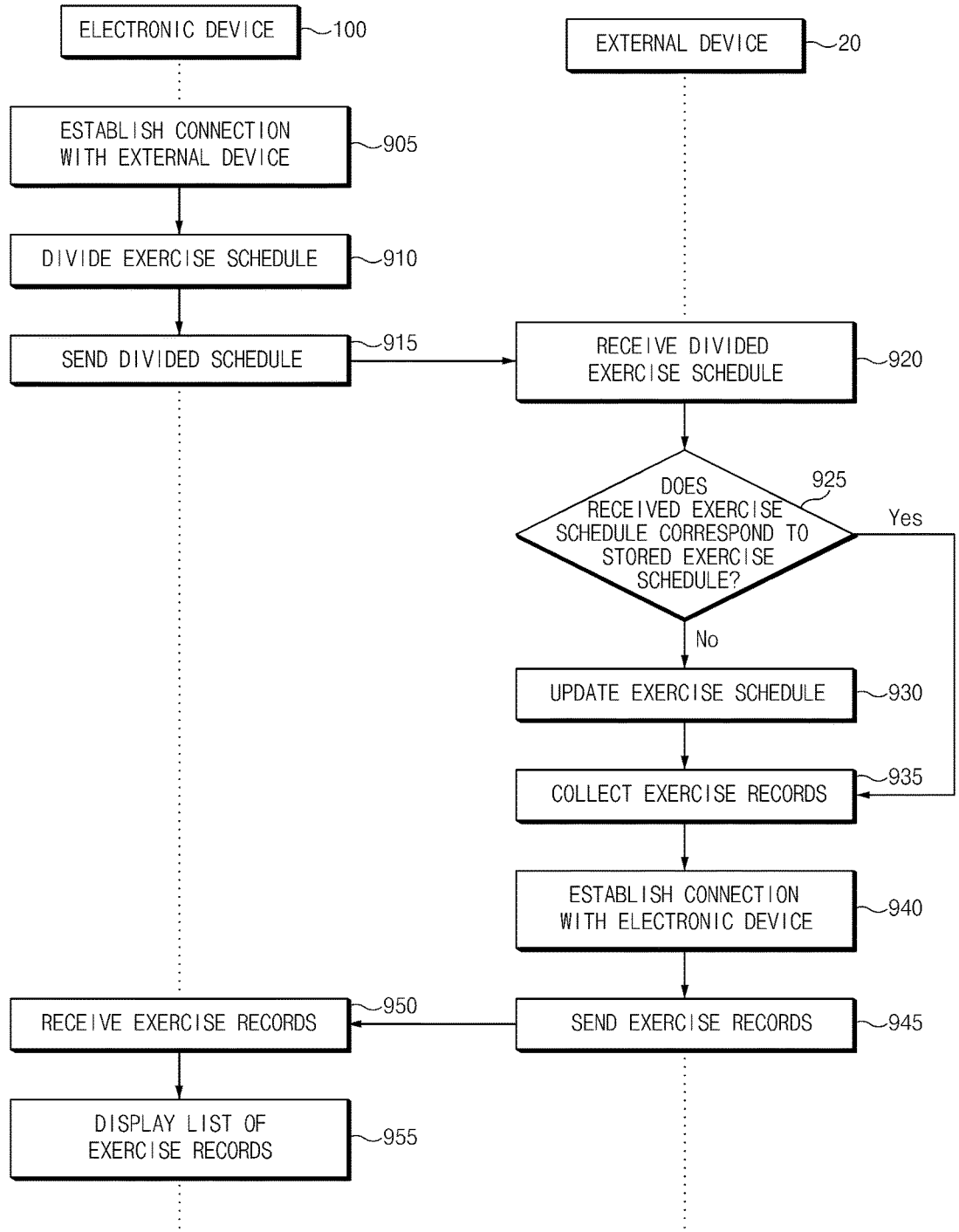
FIG. 9 is a signal sequence diagram illustrating an example method for linking an exercise method in an electronic device according to an example embodiment.

FIG. 9 is a signal sequence diagram illustrating an example method for linking an exercise method in an electronic device according to an example embodiment.

Operations illustrated in FIG. 9 may include operations processed by an electronic device 100 illustrated in FIGS. 1 and 2. Thus, although there are contents omitted below, contents described about the electronic device 100 with reference to FIGS. 1 and 2 may be applied to the operations shown in FIG. 9.

Referring to FIG. 9, in operation 905, the electronic device 100 (e.g., a processor 140 of FIG. 2) may establish a connection with the external device 20. The electronic device 100 may connect wirelessly with the external device 20 in in the same manner as, for example, Bluetooth low energy (BLE) or wireless-fidelity (Wi-Fi) direct.

In operation 910, the electronic device 100 (e.g., the processor 140) may divide an exercise schedule. For example, if connected with the external device 20, the electronic device 100 may receive a request to transmit the exercise schedule from the external device 20. The electronic device 100 may send an acknowledge character (ACK) to the request to the external device 20. The electronic device 100 may divide the exercise schedule in response to the request. For example, the electronic device 100 may divide the exercise schedule for each date.

In operation 915, the electronic device 100 (e.g., the processor 140) may send the divided exercise schedule to the external device 20. The electronic device 100 may select some of the divided exercise schedules. For example, the electronic device 100 may select an exercise schedule corresponding to a current date. For another example, the electronic device 100 may select an exercise schedule with the earliest schedule (e.g., an exercise schedule on day 4 if an exercise schedule on day 3 is performed) among exercise schedules which are not performed yet. The electronic device 100 may send the selected exercise schedule to the external device 20 through wireless communication.

In operation 920, the external device 20 may receive the divided exercise schedule from the electronic device 100. The external device 20 may store the received exercise schedules. The external device 20 may verify integrity of the received exercise schedules. For example, the external device 20 may verify whether the exercise schedule includes all of specified fields. Also, the external device 20 may verify whether a field value included in each of the specified fields is included in a normal range. If the exercise schedule includes all of the specified fields and if the field value is included in the normal range, the external device 20 may determine that there is no defect in the received exercise schedule. If verifying the integrity of the exercise schedule, the external device 20 may send an ACK to receiving the exercise schedule to the electronic device 100. If the ACK is sent, the electronic device 100 and the external device 20 may disconnect from each other.

In operation 925, the external device 20 may determine whether the received exercise schedule corresponds to a stored exercise schedule. The external device 20 may determine whether the received exercise schedule is identical to an exercise schedule previously stored before receiving the exercise schedule. If the exercise schedule is identical to the previously stored exercise schedule, the external device 20 may perform operation 935. If the exercise schedule is different from the previously stored exercise schedule, the external device 20 may perform operation 930.

If the received exercise schedule does not correspond to the previously stored exercise schedule, in operation 930, the external device 20 may update the exercise schedule. The external device 20 may store the received exercise schedule together with the previously stored exercise schedule.

In operation 935, the external device 20 may collect exercise records. The external device 20 may collect exercise records detected as its user performs exercise. The external device 20 may collect various exercise records, for example, a movement distance, a movement speed, movement acceleration, a heart rate, the number of steps, or the like using a global positioning system (GPS) module, a sensor, or the like. The external device 20 may collect exercise records in a location where it is impossible to communicate with the electronic device 100 in the same manner as BLE or Wi-Fi direct. The external device 20 may store the collected exercise records.

In operation 940, the external device 20 may establish a connection with the electronic device 100. The external device 20 may connect wirelessly with the electronic device 100 in the same manner as, for example, BLE or Wi-Fi direct. The external device 20 may connect with the electronic device 100 in a different manner from the manner used in operation 905.

In operation 945, the external device 20 may send the exercise records to the electronic device 100. For example, the external device 20 may receive a request to send exercise records from the electronic device 100. If receiving the request, the external device 20 may send an ACK to the request to the electronic device 100. The external device 20 may send the exercise records to the electronic device 100 through wireless communication.

In operation 950, the electronic device 100 (e.g., the processor 140) may receive the exercise records from the external device 20. If receiving the exercise records, the electronic device 100 may send an ACK to the reception to the external device 20.

In operation 955, the electronic device 100 (e.g., the processor 140) may display a list of the exercise records. As described above with reference to FIG. 5, the electronic device 100 may display the list of the exercise records in various manners.

Figure 10:
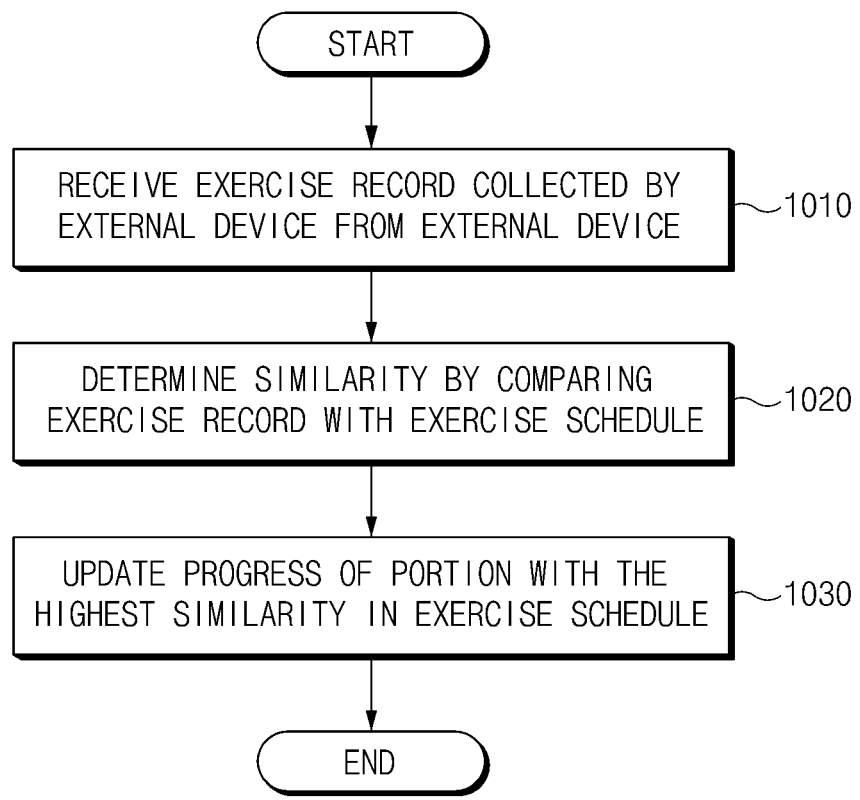
FIG. 10 is a flowchart illustrating an example method for linking an exercise method in an electronic device according to an example embodiment.

FIG. 10 is a flowchart illustrating an example method for linking an exercise method in an electronic device according to an example embodiment.

Operations illustrated in FIG. 10 may include operations processed by an electronic device 100 illustrated in FIGS. 1 and 2. Thus, although there are contents omitted below, contents described about the electronic device 100 with reference to FIGS. 1 and 2 may be applied to the operations shown in FIG. 10.

According to an embodiment, if receiving an exercise record from an external device, an electronic device may compare the exercise record with an exercise schedule and may update progress of a portion with the highest similarity to the exercise record in the exercise record.

Referring to FIG. 10, in operation 1010, the electronic device (e.g., a processor 140 of FIG. 2) may receive an exercise record collected by the external device from the external device. A user of the electronic device may carry the external device and may perform exercise in a state where an exercise schedule is not sent from the electronic device to the external device (e.g., if the electronic device does not communicate with the external device in a time set to transmit the exercise schedule). The external device may collect the exercise schedule in a state where the exercise schedule is not received. If connected with the external device, the electronic device may receive the exercise record from the external device.

In operation 1020, the electronic device (e.g., the processor 140) may determine similarity by comparing the exercise record with the exercise schedule. The exercise schedule may include a schedule having various goals, for example, 5 km running on day 1 for 30 minutes, 8 km running on day 2 for 40 minutes, and 10 km running on day 3 for 1 hour. If receiving an exercise record in which the user runs a distance of 8.1 kilometers for 45 minutes, the electronic device may filter an exercise schedule (e.g., an exercise schedule on day 3) in which a threshold value for achieving a goal is greater than a value included in the received exercise record among exercise schedules. The electronic device may determine similarity by comparing a threshold value for achieving a goal of the remaining exercise schedules (e.g., exercise schedules on days 1 and 2) with a value (e.g., an exercise time, an exercise distance, an exercise speed, or the like) included in the exercise record. In this case, the highest similarity between the exercise record and an exercise schedule (e.g., the exercise schedule on day 2) with the closest threshold value may be calculated.

In operation 1030, the electronic device (e.g., the processor 140) may update progress of a portion with the highest similarity in the exercise schedule. The electronic device may determine that the portion with the highest similarity in the exercise schedule is performed. For example, the electronic device may update progress of the exercise schedule on day 2.

As described above, exercise according to the exercise schedule may be continuously performed by matching the exercise record collected in a state where the exercise schedule is not sent to the external device with the exercise schedule.

According to an example embodiment, a method for linking an exercise schedule in an electronic device may include dividing the exercise schedule into a plurality of segments if the electronic device connects with an external device through wireless communication, sending a segment automatically selected from among the plurality of segments to the external device based on at least one of a policy defined in the electronic device or attributes of the external device, and receiving an exercise record collected by the external device from the external device if the electronic device connects with the external device again through the wireless communication after the wireless communication is disconnected.

According to an example embodiment, the dividing of the exercise schedule may include dividing the exercise schedule into the plurality of segments based on capacity, a date, or a type of exercise.

According to an example embodiment, a method for linking an exercise schedule in an electronic device may include verifying attributes information of at least one external electronic device operatively connected with the electronic device using a communication circuit of the electronic device, selecting part of schedule information based on the at least attributes information using a processor of the electronic device, and sending the part of the schedule information to the at least one external electronic device using the communication circuit.

Figure 11:
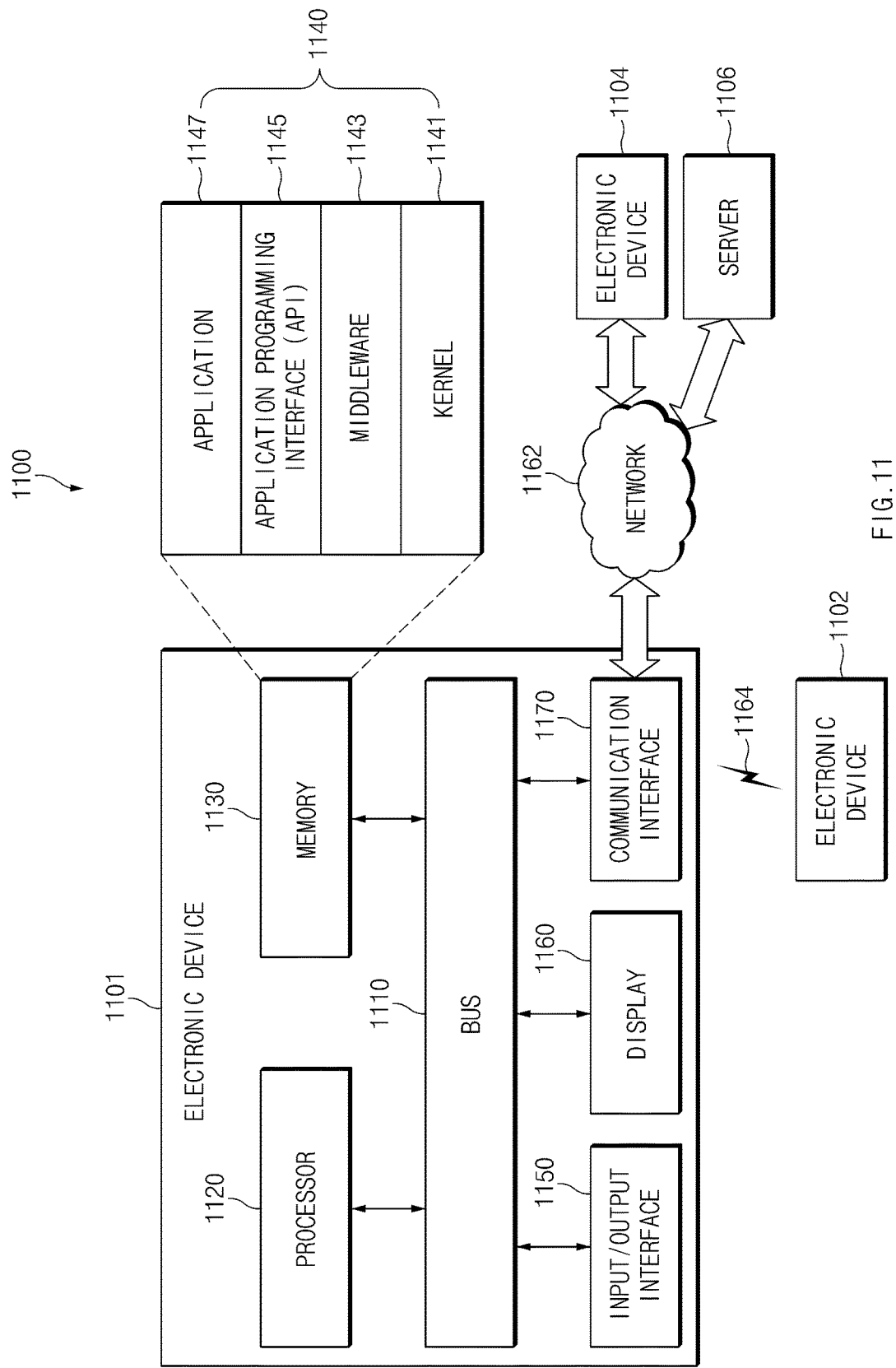
FIG. 11 is a block diagram illustrating an example configuration of an electronic device in a network environment according to various example embodiments.

FIG. 11 is a block diagram illustrating an example configuration of an electronic device in a network environment 1100 according to various example embodiments.

Referring to FIG. 11, in various embodiments, an electronic device 1101 may connect with a first external electronic device 1102 over local-area communication 1164 or may connect with a second external electronic device 1104 or a server 1106 over a network 1162. The electronic device 1101 may include a bus 1110, a processor (e.g., including processing circuitry) 1120, a memory 1130, an input/output (I/O) interface (e.g., including input/output circuitry) 1150, a display 1160, and a communication interface (e.g., including communication circuitry) 1170. In various embodiments, at least one of the components of the electronic device 1101 may be omitted from the electronic device 1101, and other components may be additionally included in the electronic device 1101.

The bus 1110 may include, for example, a circuit which connects the components 1120 to 1170 with each other and sends communication (e.g., a control message and/or data) between the components 1120 to 1170.

The processor 1120 may include various processing circuitry, such as, for example, and without limitation, one or more of a dedicated processor, a central processing unit (CPU), an application processor (AP), or a communication processor (CP). The processor 1120 may perform, for example, calculation or data processing about control and/or communication of at least another of the components of the electronic device 1101.

The memory 1130 may include a volatile and/or non-volatile memory. The memory 1130 may store, for example, a command or data associated with at least another of the components of the electronic device 1101. According to an embodiment, the memory 1130 may software and/or a program 1140. The program 1140 may include, for example, a kernel 1141, a middleware 1143, an application programming interface (API) 1145, and/or at least one application program 1147 (or "at least one application"), and the like. At least part of the kernel 1141, the middleware 1143, or the API 1145 may be referred to as an operating system (OS).

The kernel 1141 may control or manage, for example, system resources (e.g., the bus 1110, the processor 1120, or the memory 1130, and the like) used to execute an operation or function implemented in the other programs (e.g., the middleware 1143, the API 1145, or the application program 1147). Also, as the middleware 1143, the API 1145, or the application program 1147 accesses a separate component of the electronic device 1101, the kernel 1141 may provide an interface which may control or manage system resources.

The middleware 1143 may play a role as, for example, a go-between such that the API 1145 or the application program 1147 communicates with the kernel 1141 to communicate data with the kernel 1141.

Also, the middleware 1143 may process one or more work requests, received from the at least one application program 1147, in order of priority. For example, the middleware 1143 may assign priority which may use system resources (the bus 1110, the processor 1120, or the memory 1130, and the like) of the electronic device 1101 to at least one of the at least one application program 1147. For example, the middleware 1143 may perform scheduling or load balancing for the one or more work requests by processing the one or more work requests in order of priority assigned to the at least one of the at least one application program 1147.

The API 1145 may be, for example, an interface in which the application program 1147 controls a function provided from the kernel 1141 or the middleware 1143. For example, the API 1145 may include at least one interface or function (e.g., a command) for file control, window control, image processing, or text control, and the like.

The I/O interface 1150 may include various input/output circuitry and play a role as, for example, an interface which may send a command or data, input from a user or another external device, to another component (or other components) of the electronic device 1101. Also, the I/O interface 1150 may output a command or data, received from another component (or other components) of the electronic device 1101, to the user or the other external device.

The display 1160 may include, for example, a liquid crystal display (LCD), a light emitting diode (LED) display, an organic LED (OLED) display, a microelectromechanical systems (MEMS) display, or an electronic paper display, or the like, but is not limited thereto. The display 1160 may display, for example, a variety of content (e.g., text, an image, a video, an icon, or a symbol, and the like) to the user. The display 1160 may include a touch screen, and may receive, for example, a touch, a gesture, proximity, or a hovering input using an electronic pen or part of a body of the user.

The communication interface 1170 may include various communication circuitry and establish communication between, for example, the electronic device 1101 and an external device (e.g., the first external electronic device 1102, the second external electronic device 1104, or the server 1106). For example, the communication interface 1170 may connect to the network 1162 through wireless communication or wired communication and may communicate with the external device (e.g., the second external electronic device 1104 or the server 1106).

The wireless communication may use, for example, at least one of long term evolution (LTE), LTE-advanced (LTE-A), code division multiple access (CDMA), wideband CDMA (WCDMA), universal mobile telecommunications system (UMTS), wireless broadband (WiBro), or global system for mobile communications (GSM), and the like as a cellular communication protocol. Also, the wireless communication may include, for example, the local-area communication 1164. The local-area communication 1164 may include, for example, at least one of wireless-fidelity (Wi-Fi) communication, Bluetooth (BT) communication, near field communication (NFC) communication, magnetic stripe transmission (MST) communication, or global navigation satellite system (GNSS) communication, and the like.

An MST module (see, e.g., FIG. 12) may generate a pulse based on transmission data using an electromagnetic signal and may generate a magnetic field signal based on the pulse. The electronic device 1101 may send the magnetic field signal to a point of sales (POS) system. The POS system may restore the data by detecting the magnetic field signal using an MST reader and converting the detected magnetic field signal into an electric signal.

The GNSS (see, e.g., FIG. 12) may include, for example, at least one of a global positioning system (GPS), a Glonass, a Beidou navigation satellite system (hereinafter referred to as "Beidou"), or a Galileo (i.e., the European global satellite-based navigation system) according to an available area or a bandwidth, and the like. Hereinafter, the "GPS" used herein may be interchangeably with the "GNSS". The wired communication may include at least one of, for example, universal serial bus (USB) communication, high definition multimedia interface (HDMI) communication, recommended standard 232 (RS-232) communication, or plain old telephone service (POTS) communication, and the like. The network 1162 may include a telecommunications network, for example, at least one of a computer network (e.g., a local area network (LAN) or a wide area network (WAN)), the Internet, or a telephone network.

Each of the first and second external electronic devices 1102 and 1104 may be the same as or different device from the electronic device 1101. According to an embodiment, the server 1106 may include a group of one or more servers. According to various embodiments, all or some of operations executed in the electronic device 1101 may be executed in another electronic device or a plurality of electronic devices (e.g., the first external electronic device 1102, the second external electronic device 1104, or the server 1106). According to an embodiment, if the electronic device 1101 should perform any function or service automatically or according to a request, it may request another device (e.g., the first external electronic device 1102, the second external electronic device 1104, or the server 1106) to perform at least part of the function or service, rather than executing the function or service for itself or in addition to the function or service. The other electronic device (e.g., the first external electronic device 1102, the second external electronic device 1104, or the server 1106) may execute the requested function or the added function and may transmit the executed result to the electronic device 1101. The electronic device 1101 may process the received result without change or additionally and may provide the requested function or service. For this purpose, for example, cloud computing technologies, distributed computing technologies, or client-server computing technologies may be used.

Figure 12:
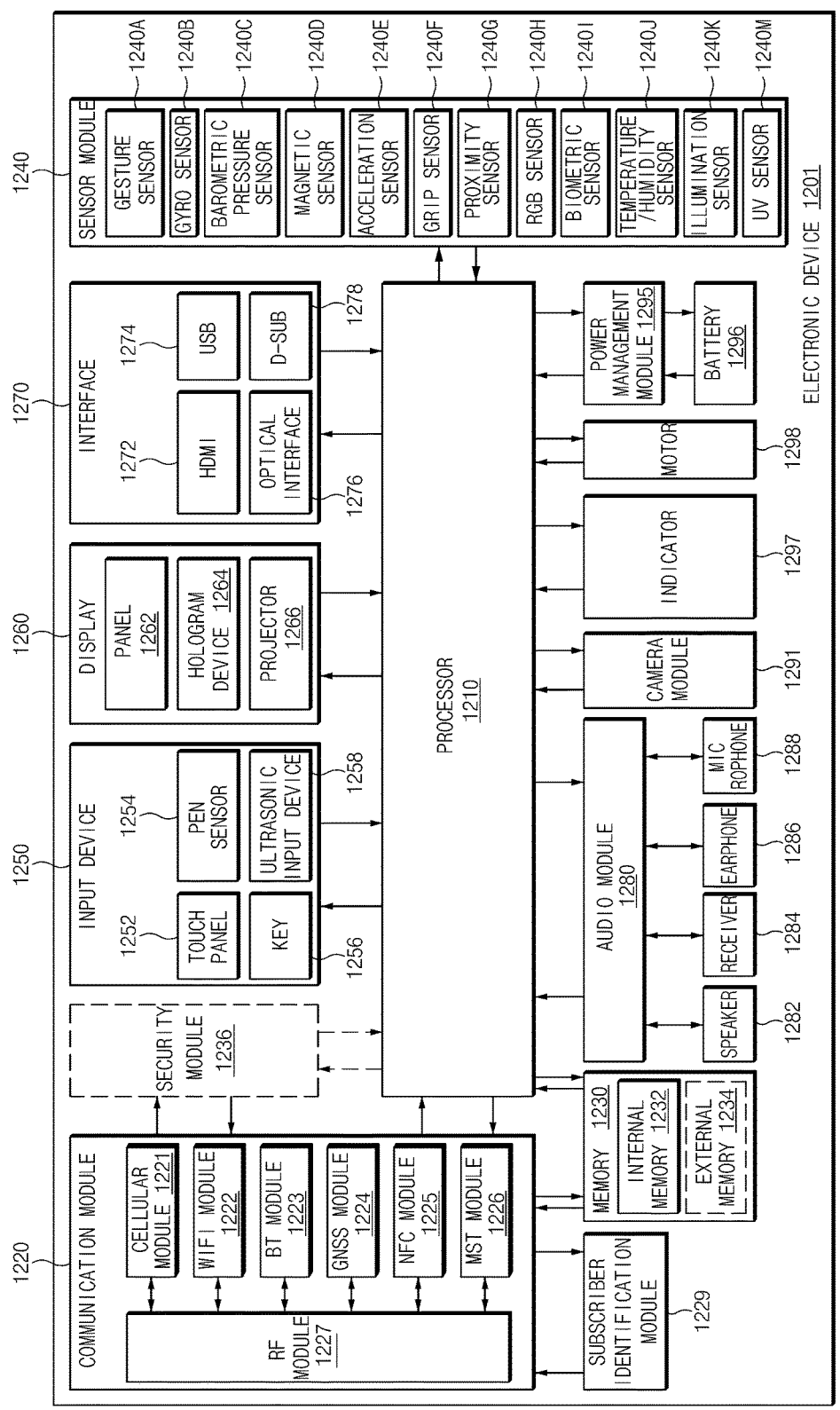
FIG. 12 is a block diagram illustrating an example configuration of an electronic device according to various example embodiments.

FIG. 12 is a block diagram illustrating an example configuration of an electronic device according to various example embodiments.

Referring to FIG. 12, an electronic device 1201 may include, for example, all or part of an electronic device 1101 illustrated in FIG. 11. The electronic device 1201 may include one or more processors 1210 (e.g., application processors (APs) and includes various processing circuitry), a communication module (e.g., including communication circuitry) 1220, a subscriber identification module (SIM) 1229, a memory 1230, a security module 1236, a sensor module 1240, an input device (e.g., including input circuitry) 1250, a display 1260, an interface (e.g., including interface circuitry) 1270, an audio module 1280, a camera module 1291, a power management module 1295, a battery 1296, an indicator 1297, and a motor 1298.

The processor 1210 may include various processing circuitry configured to execute, for example, an operating system (OS) or an application program to control a plurality of hardware or software components connected thereto and may process and compute a variety of data. The processor 1210 may be implemented with, for example, a system on chip (SoC). According to an embodiment, the processor 1210 may include a graphic processing unit (GPU) (not shown) and/or an image signal processor (not shown). The processor 1210 may include at least some (e.g., a cellular module 1221) of the components shown in FIG. 12. The processor 1210 may load a command or data, received from at least one of other components (e.g., a non-volatile memory), to a volatile memory to process the data and may store various data in a non-volatile memory.

The communication module 1220 may have the same or similar configuration to a communication interface 1170 of FIG. 11. The communication module 1220 may include various communication circuitry, such as, for example, and without limitation, the cellular module 1221, a wireless-fidelity (Wi-Fi) module 1222, a Bluetooth (BT) module 1223, a global navigation satellite system (GNSS) module 1224 (e.g., a GPS module, a Glonass module, a Beidou module, or a Galileo module), a near field communication (NFC) module 1225, an MST module 1226, and a radio frequency (RF) module 1227.

The cellular module 1221 may provide, for example, a voice call service, a video call service, a text message service, or an Internet service, and the like over a communication network. According to an embodiment, the cellular module 1221 may identify and authenticate the electronic device 1201 in a communication network using the SIM 1229 (e.g., a SIM card). According to an embodiment, the cellular module 1221 may perform at least some of functions which may be provided by the processor 1210. According to an embodiment, the cellular module 1221 may include a communication processor (CP).

The Wi-Fi module 1222, the BT module 1223, the GNSS module 1224, the NFC module 1225, or the MST module 1226 may include, for example, a processor for processing data communicated through the corresponding module. According to various embodiments, at least some (e.g., two or more) of the cellular module 1221, the Wi-Fi module 1222, the BT module 1223, the GNSS module 1224, the NFC module 1225, or the MST module 1226 may be included in one integrated chip (IC) or one IC package.

The RF module 1227 may communicate, for example, a communication signal (e.g., an RF signal). Though not shown, the RF module 1227 may include, for example, a transceiver, a power amplifier module (PAM), a frequency filter, or a low noise amplifier (LNA), or an antenna, and the like. According to another embodiment, at least one of the cellular module 1221, the Wi-Fi module 1222, the BT module 1223, the GNSS module 1224, the NFC module 1225, or the MST module 1226 may communicate an RF signal through a separate RF module.

The SIM 1229 may include, for example, a card which includes a SIM and/or an embedded SIM. The SIM 1229 may include unique identification information (e.g., an integrated circuit card identifier (ICCID)) or subscriber information (e.g., an international mobile subscriber identity (IMSI)).

The memory 1230 (e.g., a memory 1130 of FIG. 11) may include, for example, an embedded memory 1232 and/or an external memory 1234. The embedded memory 1232 may include at least one of, for example, a volatile memory (e.g., a dynamic random access memory (DRAM), a static RAM (SRAM), a synchronous dynamic RAM (SDRAM), and the like), or a non-volatile memory (e.g., a one-time programmable read only memory (OTPROM), a programmable ROM (PROM), an erasable and programmable ROM (EPROM), an electrically erasable and programmable ROM (EEPROM), a mask ROM, a flash ROM, a flash memory (e.g., a NAND flash memory or a NOR flash memory, and the like), a hard drive, or a solid state drive (SSD)).

The external memory 1234 may include a flash drive, for example, a compact flash (CF), a secure digital (SD), a micro-SD, a mini-SD, an extreme digital (xD), a multimedia card (MMC), or a memory stick, and the like. The external memory 1234 may operatively and/or physically connect with the electronic device 1201 through various interfaces.

The security module 1236 may be a module which has a relatively higher secure level than the memory 1230 and may be a circuit which stores secure data and guarantees a protected execution environment. The secure module 1236 may be implemented with a separate circuit and may include a separate processor. The security module 1236 may include, for example, an embedded secure element (eSE) which is present in a removable smart chip or a removable SD card or is embedded in a fixed chip of the electronic device 1201. Also, the security module 1236 may be driven by an OS different from the OS of the electronic device 1201. For example, the security module 1236 may operate based on a java card open platform (JCOP) OS.

The sensor module 1240 may measure, for example, a physical quantity or may detect an operation state of the electronic device 1201, and may convert the measured or detected information to an electrical signal. The sensor module 1240 may include at least one of, for example, a gesture sensor 1240A, a gyro sensor 1240B, a barometric pressure sensor 1240C, a magnetic sensor 1240D, an acceleration sensor 1240E, a grip sensor 1240F, a proximity sensor 1240G, a color sensor 1240H (e.g., red, green, blue (RGB) sensor), a biometric sensor 1240I, a temperature/humidity sensor 1240J, an illumination sensor 1240K, or an ultraviolet (UV) sensor 1240M. Additionally or alternatively, the sensor module 1240 may further include, for example, an e-nose sensor (not shown), an electromyography (EMG) sensor (not shown), an electroencephalogram (EEG) sensor (not shown), an electrocardiogram (ECG) sensor (not shown), an infrared (IR) sensor (not shown), an iris sensor (not shown), and/or a fingerprint sensor (not shown), and the like. The sensor module 1240 may further include a control circuit for controlling at least one or more sensors included therein. In various embodiments, the electronic device 1201 may further include a processor configured to control the sensor module 1240, as part of the processor 1210 or to be independent of the processor 1210. While the processor 1210 is in a sleep state, the electronic device 1201 may control the sensor module 1240.

The input device 1250 may include various input circuitry, such as, for example, and without limitation, a touch panel 1252, a (digital) pen sensor 1254, a key 1256, or an ultrasonic input unit 1258. The touch panel 1252 may use, for example, at least one of a capacitive type, a resistive type, an infrared type, or an ultrasonic type. Also, the touch panel 1252 may include a control circuit. The touch panel 1252 may further include a tactile layer and may provide a tactile reaction to a user.

According to an embodiment, the touch panel 1252 may include a pressure sensor (or a force sensor interchangeably used hereinafter) which may measure intensity of pressure on a touch of a user. The pressure sensor may be integrated with the touch panel 1252 or may be implemented with one or more sensors independent of the touch panel 1252.

The (digital) pen sensor 1254 may be, for example, part of the touch panel 1252 or may include a separate sheet for recognition. The key 1256 may include, for example, a physical button, an optical key, or a keypad. The ultrasonic input unit 1258 may allow the electronic device 1201 to detect an ultrasonic wave generated by an input tool, through a microphone (e.g., a microphone 1288) and to verify data corresponding to the detected ultrasonic wave.

The display 1260 (e.g., a display 1160 of FIG. 11) may include a panel 1262, a hologram device 1264, or a projector 1266. The panel 1262 may include the same or similar configuration to the display 1160. The panel 1262 may be implemented to be, for example, flexible, transparent, or wearable. The panel 1262 and the touch panel 1252 may be integrated into one module. The hologram device 1264 may show a stereoscopic image in a space using interference of light. The projector 1266 may project light onto a screen to display an image. The screen may be positioned, for example, inside or outside the electronic device 1201. According to an embodiment, the display 1260 may further include a control circuit for controlling the panel 1262, the hologram device 1264, or the projector 1266.

The interface 1270 may include various interface circuitry, such as, for example, and without limitation, a high-definition multimedia interface (HDMI) 1272, a universal serial bus (USB) 1274, an optical interface 1276, or a D-subminiature 1278. The interface 1270 may be included in, for example, a communication interface 1170 shown in FIG. 11. Additionally or alternatively, the interface 1270 may include, for example, a mobile high definition link (MHL) interface, an SD card/multimedia card (MMC) interface, or an infrared data association (IrDA) standard interface.

The audio module 1280 may interchangeably convert a sound into an electric signal. At least some of components of the audio module 1280 may be included in, for example, an input and output interface 1150 shown in FIG. 11. The audio module 1280 may process sound information input or output through, for example, a speaker 1282, a receiver 1284, an earphone 1286, or the microphone 1288, and the like.

The camera module 1291 may be a device which captures a still image and a moving image. According to an embodiment, the camera module 1291 may include one or more image sensors (not shown) (e.g., a front sensor or a rear sensor), a lens (not shown), an image signal processor (ISP) (not shown), or a flash (not shown) (e.g., an LED or a xenon lamp).

The power management module 1295 may manage, for example, power of the electronic device 1201. According to an embodiment, though not shown, the power management module 1295 may include a power management integrated circuit (PMIC), a charger IC or a battery or fuel gauge. The PMIC may have a wired charging method and/or a wireless charging method. The wireless charging method may include, for example, a magnetic resonance method, a magnetic induction method, or an electromagnetic method, and the like. An additional circuit for wireless charging, for example, a coil loop, a resonance circuit, or a rectifier, and the like may be further provided. The battery gauge may measure, for example, the remaining capacity of the battery 1296 and voltage, current, or temperature thereof while the battery 1296 is charged. The battery 1296 may include, for example, a rechargeable battery or a solar battery.

The indicator 1297 may display a specific state of the electronic device 1201 or part (e.g., the processor 1210) thereof, for example, a booting state, a message state, or a charging state, and the like. The motor 1298 may convert an electric signal into mechanical vibration and may generate vibration or a haptic effect, and the like. Though not shown, the electronic device 1201 may include a processing unit (e.g., a GPU) for supporting a mobile TV. The processing unit for supporting the mobile TV may process media data according to standards, for example, a digital multimedia broadcasting (DMB) standard, a digital video broadcasting (DVB) standard, or a mediaFlo™ standard, and the like.

Each of the above-mentioned elements of the electronic device according to various embodiments of the present disclosure may be configured with one or more components, and names of the corresponding elements may be changed according to the type of the electronic device. The electronic device according to various embodiments of the present disclosure may include at least one of the above-mentioned elements, some elements may be omitted from the electronic device, or other additional elements may be further included in the electronic device. Also, some of the elements of the electronic device according to various embodiments of the present disclosure may be combined with each other to form one entity, thereby making it possible to perform the functions of the corresponding elements in the same manner as before the combination.

Figure 13:
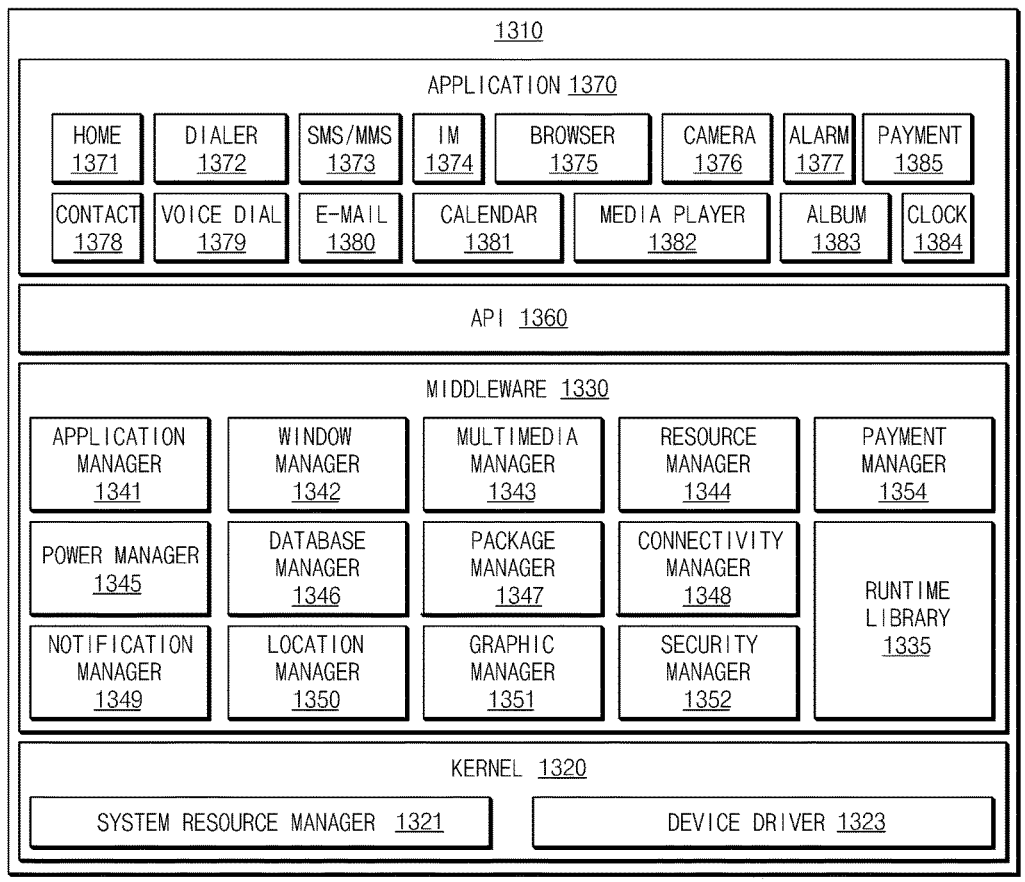
FIG. 13 is a block diagram illustrating an example configuration of a program module according to various example embodiments.

FIG. 13 is a block diagram illustrating an example configuration of a program module according to various example embodiments.

According to an embodiment, a program module 1310 (e.g., a program 1140 of FIG. 11) may include an operating system (OS) for controlling resources associated with an electronic device (e.g., an electronic device 1101 of FIG. 11) and/or various applications (e.g., at least one application program 1147 of FIG. 11) which are executed on the OS. The OS may be, for example, Android, iOS, Windows, Symbian, Tizen, or Bada, and the like.

The program module 1310 may include a kernel 1320, a middleware 1330, an application programming interface (API) 1360, and/or at least one application 1370. At least part of the program module 1310 may be preloaded on the electronic device, or may be downloaded from an external electronic device (e.g., a first external electronic device 1102, a second external electronic device 1104, or a server 1106, and the like of FIG. 11).

The kernel 1320 (e.g., a kernel 1141 of FIG. 11) may include, for example, a system resource manager 1321 and/or a device driver 1323. The system resource manager 1321 may control, assign, or collect, and the like system resources. According to an embodiment, the system resource manager 1321 may include a process management unit, a memory management unit, or a file system management unit, and the like. The device driver 1323 may include, for example, a display driver, a camera driver, a Bluetooth (BT) driver, a shared memory driver, a universal serial bus (USB) driver, a keypad driver, a wireless-fidelity (Wi-Fi) driver, an audio driver, or an inter-process communication (IPC) driver.

The middleware 1330 (e.g., a middleware 1143 of FIG. 11) may provide, for example, functions the application 1370 needs in common, and may provide various functions to the application 1370 through the API 1360 such that the application 1370 efficiently uses limited system resources in the electronic device. According to an embodiment, the middleware 1330 (e.g., the middleware 1143) may include at least one of a runtime library 1335, an application manager 1341, a window manager 1342, a multimedia manager 1343, a resource manager 1344, a power manager 1345, a database manager 1346, a package manager 1347, a connectivity manager 1348, a notification manager 1349, a location manager 1350, a graphic manager 1351, a security manager 1352, or a payment manager 1354.

The runtime library 1335 may include, for example, a library module used by a compiler to add a new function through a programming language while the application 1370 is executed. The runtime library 1335 may perform a function about input and output management, memory management, or an arithmetic function.

The application manager 1341 may manage, for example, a life cycle of at least one of the at least one application 1370. The window manager 1342 may manage graphic user interface (GUI) resources used on a screen of the electronic device. The multimedia manager 1343 may ascertain a format necessary for reproducing various media files and may encode or decode a media file using a codec corresponding to the corresponding format. The resource manager 1344 may manage source codes of at least one of the at least one application 1370, and may manage resources of a memory or a storage space, and the like.

The power manager 1345 may act together with, for example, a basic input/output system (BIOS) and the like, may manage a battery or a power source, and may provide power information necessary for an operation of the electronic device. The database manager 1346 may generate, search, or change a database to be used in at least one of the at least one application 1370. The package manager 1347 may manage installation or update of an application distributed by a type of a package file.

The connectivity manager 1348 may manage, for example, wireless connection such as Wi-Fi connection or BT connection, and the like. The notification manager 1349 may display or notify events, such as an arrival message, an appointment, and proximity notification, by a method which is not disturbed to the user. The location manager 1350 may manage location information of the electronic device. The graphic manager 1351 may manage a graphic effect to be provided to the user or a user interface (UI) related to the graphic effect. The security manager 1352 may provide all security functions necessary for system security or user authentication, and the like. According to an embodiment, when the electronic device (e.g., the electronic device 1101) has a phone function, the middleware 1330 may further include a telephony manager (not shown) for managing a voice or video communication function of the electronic device.

The middleware 1330 may include a middleware module which configures combinations of various functions of the above-described components. The middleware 1330 may provide a module which specializes according to kinds of OSs to provide a differentiated function. Also, the middleware 1330 may dynamically delete some of old components or may add new components.

The API 1360 (e.g., an API 1145 of FIG. 11) may be, for example, a set of API programming functions, and may be provided with different components according to OSs. For example, in case of Android or iOS, one API set may be provided according to platforms. In case of Tizen, two or more API sets may be provided according to platforms.

The application 1370 (e.g., an application program 1147 of FIG. 11) may include one or more of, for example, a home application 1371, a dialer application 1372, a short message service/multimedia message service (SMS/MMS) application 1373, an instant message (IM) application 1374, a browser application 1375, a camera application 1376, an alarm application 1377, a contact application 1378, a voice dial application 1379, an e-mail application 1380, a calendar application 1381, a media player application 1382, an album application 1383, a clock application 1384, a payment application 1385, a health care application (e.g., an application for measuring quantity of exercise or blood sugar, and the like), or an environment information application (e.g., an application for providing atmospheric pressure information, humidity information, or temperature information, and the like), and the like.

According to an embodiment, the application 1370 may include an application (hereinafter, for better understanding and ease of description, referred to as "information exchange application") for exchanging information between the electronic device (e.g., the electronic device 1101) and an external electronic device (e.g., the first external electronic device 1102 or the second external electronic device 1104). The information exchange application may include, for example, a notification relay application for transmitting specific information to the external electronic device or a device management application for managing the external electronic device.

For example, the notification relay application may include a function of transmitting notification information, which is generated by other applications (e.g., the SMS/MMS application, the e-mail application, the health care application, or the environment information application, and the like) of the electronic device, to the external electronic device (e.g., the first external electronic device 1102 or the second external electronic device 1104). Also, the notification relay application may receive, for example, notification information from the external electronic device, and may provide the received notification information to the user of the electronic device.

The device management application may manage (e.g., install, delete, or update), for example, at least one (e.g., a function of turning on/off the external electronic device itself (or partial components) or a function of adjusting brightness (or resolution) of a display) of functions of the external electronic device (e.g., the first external electronic device 1102 or the second external electronic device 1104) which communicates with the electronic device, an application which operates in the external electronic device, or a service (e.g., a call service or a message service) provided from the external electronic device.

According to an embodiment, the application 1370 may include an application (e.g., the health card application of a mobile medical device) which is preset according to attributes of the external electronic device (e.g., the first external electronic device 1102 or the second external electronic device 1104). According to an embodiment of the present disclosure, the application 1370 may include an application received from the external electronic device (e.g., the server 1106, the first external electronic device 1102, or the second external electronic device 1104). According to an embodiment of the present disclosure, the application 1370 may include a preloaded application or a third party application which may be downloaded from a server. Names of the components of the program module 1310 according to various embodiments of the present disclosure may differ according to kinds of OSs.

According to various embodiments, at least part of the program module 1310 may be implemented with software, firmware, hardware, or at least two or more combinations thereof. At least part of the program module 1310 may be implemented (e.g., executed) by, for example, a processor (e.g., a processor 1210 of FIG. 12). At least part of the program module 1310 may include, for example, a module, a program, a routine, sets of instructions, or a process, and the like for performing one or more functions.

The terminology "module" used herein may refer, for example, to a unit including one of hardware, software, and firmware or two or more combinations thereof. The terminology "module" may be interchangeably used with, for example, terminologies "unit", "logic", "logical block", "component", or "circuit", and the like. The "module" may be a minimum unit of an integrated component or a part thereof. The "module" may be a minimum unit performing one or more functions or a part thereof. The "module" may be mechanically or electronically implemented. For example, the "module" may include at least one of processing circuitry, a dedicated processor, a CPU, an application-specific integrated circuit (ASIC) chip, field-programmable gate arrays (FPGAs), or a programmable-logic device, which is well known or will be developed in the future, for performing certain operations.

According to various embodiments, at least part of a device (e.g., modules or the functions) or a method (e.g., operations) may be implemented with, for example, instructions stored in computer-readable storage media which have a program module. When the instructions are executed by a processor (e.g., a processor 1120 of FIG. 11), one or more processors may perform functions corresponding to the instructions. The computer-readable storage media may be, for example, a memory 1130 of FIG. 11.

The computer-readable storage media may include a hard disc, a floppy disk, magnetic media (e.g., a magnetic tape), optical media (e.g., a compact disc read only memory (CD-ROM) and a digital versatile disc (DVD)), magneto-optical media (e.g., a floptical disk), a hardware device (e.g., a ROM, a random access memory (RAM), or a flash memory, and the like), and the like. Also, the program instructions may include not only mechanical codes compiled by a compiler but also high-level language codes which may be executed by a computer using an interpreter and the like. The above-mentioned hardware device may be configured to operate as one or more software modules to perform operations according to various embodiments of the present disclosure, and vice versa.

According to various embodiments, a computer-readable storage media may store instructions executed by at least one processor. The instructions may be configured to, when executed by the processor, cause a computer to divide an exercise schedule into a plurality of segments if an electronic device connects with an external device through wireless communication, send a segment automatically selected from among a plurality of segments to the external device based on at least one of a policy defined in the electronic device or attributes of the external device, and receive an exercise record collected by the external device from the external device if the electronic device connects with the external device again through the wireless communication after the wireless communication is disconnected.

According to various embodiments, a computer-readable storage media may store instructions executed by at least one processor. The instructions may be configured to, when executed by the processor, verify attribute information of at least one external electronic device operatively connected with an electronic device using a communication circuit of the electronic device, select part of schedule information based on at least the attribute information using a processor of the electronic device, and send the part of the schedule information to the at least one external electronic device using the communication circuit.

Modules or program modules according to various embodiments may include at least one or more of the above-mentioned components, some of the above-mentioned components may be omitted, or other additional components may be further included. Operations executed by modules, program modules, or other components may be executed by a successive method, a parallel method, a repeated method, or a heuristic method. Also, some operations may be executed in a different order or may be omitted, and other operations may be added.

According to various example embodiments, the electronic device may effectively collect the exercise record corresponding to the exercise schedule using the external device having limited performance by dividing the exercise schedule based on criteria.

According to various example embodiments, the electronic device may send a requested exercise schedule to the external device without the operation of the user by automatically selecting some of a plurality of segments included in the exercise schedule.

In addition, according to various example embodiments, the electronic device may provide various effects directly or indirectly ascertained through the present disclosure.

Various example embodiments of the present disclosure described and illustrated in the drawings are provided as examples to describe technical content and aid in understanding but do not limit the scope of the present disclosure. Accordingly, it should be understood that all modifications or modified forms derived based on the technical ideas of the present disclosure are included in the scope of the present disclosure as defined in the claims, and their equivalents.

What is claimed is:

1. A method for linking an exercise schedule in an electronic device, the method comprising:
    connecting with a wearable device through wireless communication;
    in response to connecting with the wearable device, transmitting a segment at a specified interval to the wearable device such that the wearable device stores the segment;
    reconnecting with the wearable device through the wireless communication after the wireless communication is disconnected; and
    in response to the reconnecting, receiving an exercise record, corresponding to the transmitted segment, collected by the wearable device from the wearable device,
    wherein the transmitting the segment at the specified interval comprises: dividing the exercise schedule at the specified interval into a plurality of segments; and selecting the segment from among the plurality of segments based on attributes of the wearable device.

2. The method of claim 1, wherein the dividing of the exercise schedule comprises:
    dividing the exercise schedule into the plurality of segments based on a capacity, a date, or a type of exercise.

3. An electronic device, comprising:
    a communication circuit;
    a memory configured to store schedule information associated with user activity; and
    a processor,
    wherein the processor is configured to:
    connect with at least one wearable electronic device through wireless communication;
    in response to connecting with the at least one wearable device, transmit part of the schedule information at a specified interval to the at least one wearable device such that the wearable device stores the part of the schedule information,
    re-connect with the at least one wearable device through the wireless communication after the wireless communication is disconnected, and
    in response to the reconnecting, receive an exercise record, corresponding to the part of the schedule information, collected by the at least one wearable electronic device from the at least one wearable electronic device,
    wherein the processor is further configured to, in order to transmit the part of the schedule information, divide the schedule information at the specified interval, verify attribute information of the at least one wearable electronic device, and select the part of the schedule information based on the attribute information.

4. The electronic device of claim 3, wherein the attribute information comprises at least part of a type, a category, a model name, or a capacity, associated with the at least one wearable electronic device.

5. The electronic device of claim 3, wherein the processor is configured to:
    select the part of the schedule information further based on context information of a user of the electronic device.

6. The electronic device of claim 3, wherein the processor is configured to:

select a first part of the schedule information as the part of the schedule information, if the attribute information corresponds to first attribute information; and select a second part of the schedule information as the part of the schedule information, if the attribute information corresponds to second attribute information.

7. The electronic device of claim 3, wherein the at least one wearable electronic device comprises a first wearable electronic device and a second wearable electronic device, and wherein the processor is configured to:

obtain first information associated with the user activity from the first wearable electronic device;

obtain second information associated with the user activity from the second wearable electronic device; and provide at least part of the first information or the second information using a display operatively connected with the electronic device.

8. An electronic device, comprising:

a communication circuit configured to perform wireless communication;

a memory configured to store an exercise schedule capable of being divided into a plurality of segments; and a processor configured to electrically connect with the communication circuit and the memory, wherein the processor is configured to:

connect with a wearable device through wireless communication, in response to connecting with the wearable device, transmit a segment at a specified interval to the wearable device such that the wearable device stores the segment, reconnect with the wearable device through the wireless communication after the wireless communication is disconnected; and in response to the reconnecting, receive an exercise record, corresponding to the transmitted segment, collected by the wearable device from the wearable device, wherein the processor is further configured to, in order to transmit the segment, divide the exercise schedule at the specified interval into the plurality of segments and select the segment from among the plurality of segments based on attributes of the wearable device.

9. The electronic device of claim 8, wherein the processor is configured to:

divide the exercise schedule into the plurality of segments based on the at least one of the policy defined in the electronic device or the attributes of the wearable device.

10. The electronic device of claim 9, wherein the processor is configured to:

divide the exercise schedule into the plurality of segments based on a capacity, a date, or a type of exercise.

11. The electronic device of claim 8, wherein the processor is configured to:

convert the selected segment into a predetermined structure to secure integrity for the selected segment; and send the converted segment to the wearable device.

12. The electronic device of claim 8, wherein the processor is configured to:

compare the exercise record with the exercise schedule, if receiving the exercise record from the wearable device; and update progress of a portion having a highest similarity to the exercise record in the exercise schedule.

13. The electronic device of claim 8, wherein the processor is configured to:

update progress of the exercise schedule based on the exercise record.

14. The electronic device of claim 13, further comprising:

a display configured to electrically connect with the processor, wherein the processor is configured to:

display the exercise record or the progress of the exercise schedule on the display.

15. The electronic device of claim 8, further comprising:

a display configured to electrically connect with the processor, wherein the processor is configured to:

display a reward associated with the exercise record or the exercise schedule on the display.

16. The electronic device of claim 8, wherein the communication circuit is configured to:

perform wireless communication with a plurality of wearable devices comprising a first wearable device and a second wearable device, and wherein the processor is configured to:

update progress of the exercise schedule based on a first exercise record, if receiving the first exercise record from the first wearable device, and send the first exercise record to the second wearable device using the communication circuit;

update progress of the exercise schedule based on a second exercise record, if receiving the second exercise record from the second wearable device, and send the second exercise record to the first wearable device using the communication circuit.

17. The electronic device of claim 8, further comprising:

a display configured to electrically connect with the processor, wherein the communication circuit is configured to:

perform wireless communication with a plurality of wearable devices, and wherein the processor is configured to:

display the exercise record or progress of the exercise schedule on the display to identify a wearable device transmitting the exercise record from among the plurality of wearable devices.

18. The electronic device of claim 8, wherein the processor is configured to:

send the exercise record or progress of the exercise schedule to a server using the communication circuit.

19. The electronic device of claim 8, wherein the processor is configured to:

receive the exercise schedule from a server using the communication circuit, if the exercise schedule in the electronic device is deleted or damaged.

* * * * *